United States Patent [19]
Knaebel

[11] Patent Number: 5,511,409
[45] Date of Patent: Apr. 30, 1996

[54] MEASUREMENT OF EMISSION LEVELS IN A GAS STREAM

[76] Inventor: Kent S. Knaebel, 8000 McKitrick Rd., Plain City, Ohio 43064

[21] Appl. No.: 308,668

[22] Filed: Sep. 19, 1994

[51] Int. Cl.⁶ ............................. B01D 53/04; B01D 53/30
[52] U.S. Cl. ...................... 73/28.04; 73/28.01; 73/31.03
[58] Field of Search ..................... 73/28.04, 28.01, 73/31.03, 31.07, 29.01; 55/28, 23

[56] References Cited

U.S. PATENT DOCUMENTS

| | | | |
|---|---|---|---|
| 3,768,302 | 10/1973 | Barringer | 78/28 |
| 3,841,145 | 10/1974 | Boubel | 73/28 |
| 3,922,905 | 12/1975 | Roth | 73/28 |
| 4,133,202 | 1/1979 | Marple | 73/28 |
| 4,388,272 | 6/1983 | Gesteland | 422/102 |
| 4,480,393 | 11/1984 | Flink et al. | 34/27 |
| 4,534,230 | 8/1985 | Courbon | 73/863.23 |
| 4,787,052 | 11/1988 | Yamaguchi | 364/550 |
| 5,032,150 | 7/1991 | Knaebel | 55/20 |
| 5,110,747 | 5/1992 | Pataschnick et al. | 436/133 |
| 5,152,812 | 10/1992 | Kovach | 55/23 |
| 5,196,170 | 3/1993 | Pataschnick et al. | 422/83 |
| 5,198,001 | 3/1993 | Knebel et al. | 55/28 |
| 5,223,439 | 6/1993 | Rolle et al. | 436/177 |
| 5,267,897 | 12/1993 | Drees | 454/229 |
| 5,377,532 | 1/1995 | Urza | 73/73 |

OTHER PUBLICATIONS

"Temperature Front Sensing for Feed Step Control in Pressure Swing Adsorption" I&EC Research, 1987 Matz et al.
High–Volume Air Sampler for Particle and Gas Sampling.2. Use of back–up Filters to Correct for the Adsorption . . . Hart, et al., 1994 Am. Chem. Soc., Environ. Sci. Technol. vol. 28, No. 4, 1994.

Primary Examiner—Hezron E. Williams
Assistant Examiner—J. David Wiggins
Attorney, Agent, or Firm—Mueller and Smith

[57] ABSTRACT

System and method for monitoring the level of a VOC or other vapor contaminant emitted in a gas stream or the like being vented at a specified pressure from an emission source. A medium of a bed of solid particles is provided within a vessel having an inlet and an outlet which is effective for separating the contaminant from the gas stream. The inlet pressure of the vessel is maintained at the specified pressure of the gas stream being vented from the emission source. The separated contaminants are concentrated in the medium which exhibits an increase in mass corresponding to the amount of the contaminant that was contained in the gas stream.

34 Claims, 8 Drawing Sheets

MEASUREMENT OF EMISSION LEVELS IN A GAS STREAM

BACKGROUND OF THE INVENTION

The present invention relates broadly to the measurement of emission levels in a gas stream, and more particularly to a system and method for monitoring the level of a VOC or other vapor or solid contaminant being emitted in a vented gas stream or the like.

The widespread use of solvents and the like in industrial applications has resulted in increased emissions of volatile organic compounds (VOCs) into the atmosphere, giving rise to environmental concerns and prompting stricter legislative controls on these emissions. One such control promulgated at the federal level is the Clean Air Act of 1977. This Act, along with its 1990 and 1991 amendments, mandates that industry monitor air pollutants, maintain emission records, and make such records available to officials of the Environmental Protection Agency, the federal agency charged with enforcement of the Act. As a consequence, manufacturers of pharmaceuticals, coated products, textiles, and polymer composites and foams, as well as hydrocarbon producers and distributors, have sought improvements both in the methods for removing VOCs from process gas streams, and for monitoring the levels of VOCs that are emitted to ensure that such levels are within prescribed limits.

One method for removing VOCs from process gas streams is disclosed in U.S. Pat. Nos. 4,480,393 and 5,152,812. By first concentrating the condensable vapors contained in a process gas stream carrier and then employing refrigeration condensation to effect their recovery, the method operates more energy efficiently than those methods previously known. Particularly, this method entails first passing a process gas stream carrying a condensable organic compound such as a solvent through, for example, a packed carbon bed which adsorbs the solvent vapor such that solvent is accumulated in the bed and a solvent-free process gas stream may be exhausted or recycled back to the process. Upon becoming saturated with adsorbed solvent, the bed is regenerated by the circulation therethrough of a heated inert gas or air stream to vaporize the solvent. Once vaporized, the solvent is carried by the gas stream from the bed to a refrigeration/condensation recovery system. Therein, the vapor-laden gas stream is passed through a turbine expander to thereby effect an expansive cooling at pressures near atmospheric to temperatures generally well below the boiling points of the solvents to be recovered. Separation of the condensable solvent vapors from the relatively non-condensable inert gas stream carrier subsequently may be effected with the recycling of recovered solvent back to the process and the recycling of inert gas back to the packed bed to continue its regeneration.

With improvements in the methods for removing VOCs from process gas streams, have come calls from industry for similar improvements in the methods heretofore known in the art for monitoring the level of VOC emissions. Prior methods have involved calculating the amount of the emission as a product of the flow rate of the gas stream being vented and the average concentration of the contaminant in the gas stream. Accordingly, both the flow rate of the gas stream and the concentration of the contaminant in the gas heretofore have had to be measured such that an average concentration could be determined. However, in most industrial processes, both the gas flow rate and contaminant concentration are time dependent. Thus, the prior methods were susceptible to concentration peaks and to unsteady-state flow in yielding sometimes spurious results. The preferred method, in contrast, would be unaffected by time dependent or localized concentration gradients, or by erratic flow. The preferred method additionally would be adaptable to the measurement of both vapor and solid phase emission, would not introduce a pressure drop or other obstruction into the flow of the emission, which pressure drop or obstruction itself would affect the emission rate or level being monitored.

In view of the foregoing, it may be seen that there has existed and remains a need for improvements in measuring the emission levels of process gas streams and the like.

BROAD STATEMENT OF THE INVENTION

The present invention relates to a system and method for monitoring the level of a VOC or other vapor or solid contaminant being emitted in a vented gas stream or the like. A medium, such as an adsorbent, a filter, or the like, is used to separate substantially all of the contaminant from a defined amount of the gas stream. The separated contaminants are concentrated in the medium which, accordingly, exhibits an increase in mass corresponding to the amount of the contaminant that was contained in the gas stream. In utilizing the medium to collect substantially all of the contaminant from the emission over a given time interval, the present invention is unaffected by concentration gradients, or by time dependent variations in the flow rate of the gas stream. Moreover, in providing for the maintaining of the pressure of the gas stream being vented, the present invention is able to compensate for any pressure drop introduced by the flow of the gas stream through the medium such that the level of the emission is not affected by the monitoring thereof.

It is, therefore, a feature of the invention to provide a method for determining the amount of a contaminant emitted in a gas stream being vented at a specified pressure. A medium is provided which is effective for separating substantially all of the contaminant from a defined amount of the gas stream. The initial mass, $m_o$, of the medium is determined, and the pressure of the gas stream being vented is maintained at the specified pressure. The defined amount of the gas stream is passed through the medium to concentrate the contaminant therein. A final mass, $m_f$, of the medium and the contaminant concentrated therein is determined, and the amount of contaminant emitted per unit time in the gas stream is determined according to the expression:

$$\frac{m_c}{t}$$

where $m_c$ is mass of the contaminant concentrated in the medium defined as the difference $m_f - m_o$.

It is a further feature of the invention to provide a system for determining the amount of a contaminant emitted in a gas stream being vented at a specified pressure. A vessel is provided as having an inlet port coupled in fluid communication with the gas stream for receiving a defined amount thereof for passage during a time interval, t, through the vessel, and an outlet port for exhausting the gas stream passed through the vessel from the vessel. A medium is disposed in the vessel for separating substantially all of the contaminant from the defined amount of the gas stream passed through the vessel. The medium has an initial mass, $m_o$, and a final mass, $m_f$, corresponding to the mass of the medium and the mass of the contaminant concentrated therein. A flow controller, such as a pump, blower, or compressor, is coupled in fluid communication with the gas stream for maintaining the pressure of the gas stream being vented at the specified pressure. The amount of contaminant emitted in the gas stream per unit time is determined according to the expression:

$$\frac{m_c}{t}$$

where $m_c$ is mass of the contaminant concentrated in the medium defined as the difference $m_f - m_o$.

It is yet a further feature of the invention to provide a system for detecting contaminants in a gas emission. A medium is provided as effective for separating at least a portion of the contaminants from the gas emission. The medium has at least one surface in fluid communication with the gas emission for concentrating the contaminants therein. A sensor assembly senses the change in mass of the medium in response to the concentration of the contaminants therein, the change in mass of the medium corresponding to the amount of the contaminants in the gas emission. The sensor assembly may be provided as having a cantilevered member extending between a fixed end and a free end supporting the medium. The cantilevered member is deflectable intermediate the fixed end and the free end in response to the change in mass of the medium. A sensor mounted on the cantilevered member is responsive to the deflection of the cantilevered member for generating output signals proportional to the mass of the medium.

Alternatively, the sensor assembly may be provided as having a diaphragm supporting the medium. The diaphragm has a fixed perimeter and a central portion within the perimeter which is deflectable in response to the change in mass of the medium. A first sensor element is mounted to the central portion of the diaphragm for movement in correspondence with the deflection thereof, and a second sensor element is fixed a predetermined distance from the first sensor element to confront the movement thereof. The first and second sensor elements are responsive to the distance therebetween for generating output signals proportional to the mass of the medium.

The invention, accordingly, comprises the system and method possessing the construction, combination of elements, and arrangement of parts and steps which are exemplified in the following detailed description. Reference to that description and to the accompanying drawings should be had for a fuller understanding and appreciation of the nature and objects of the invention, although other objects may be obvious to those skilled in the art.

BRIEF DESCRIPTION OF THE DRAWINGS

For a fuller understanding of the nature and objects of the invention, reference should be had to the following detailed description taken in connection with the accompanying drawings wherein.

Figure 1:
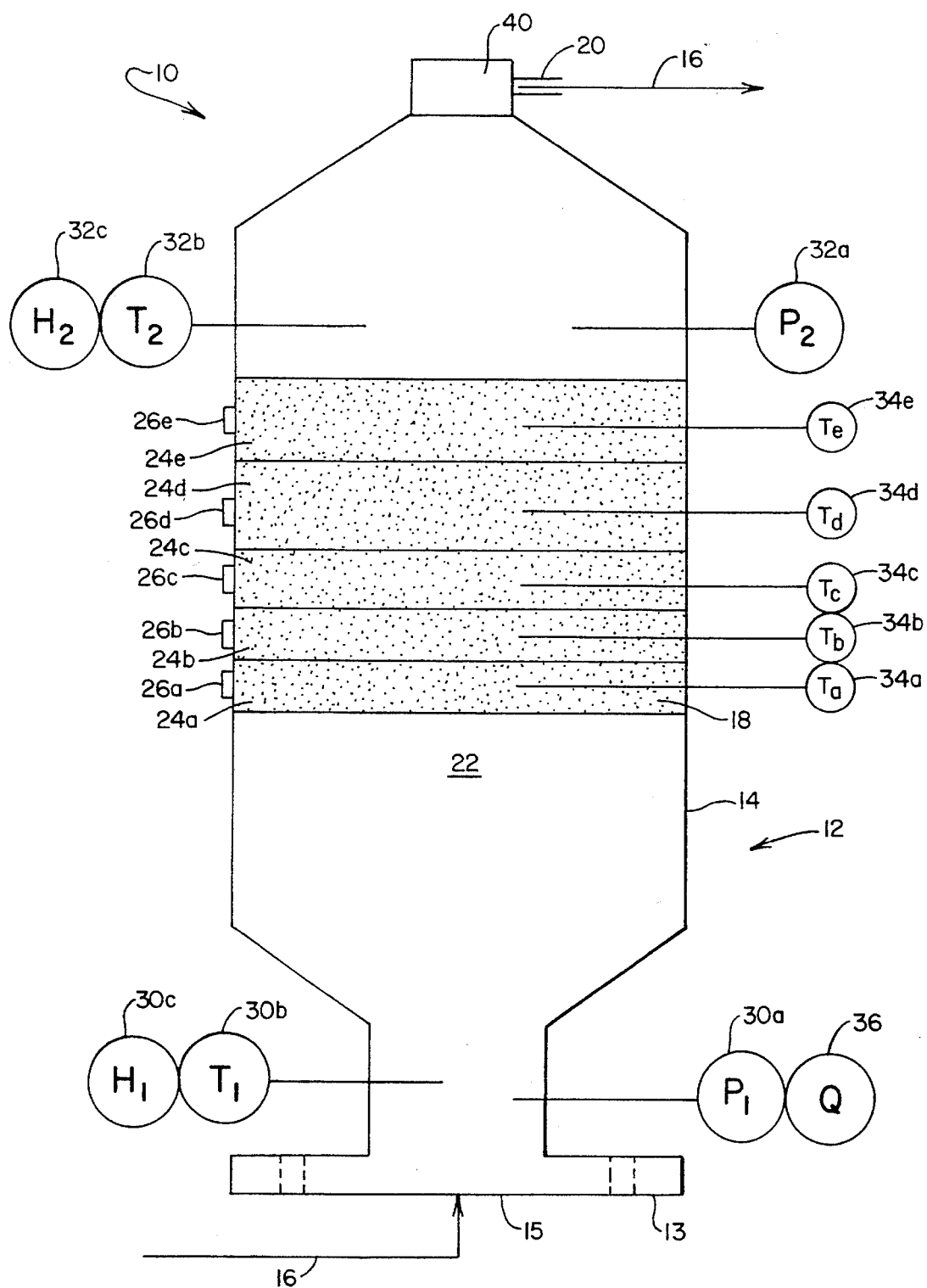
FIG. 1 is a schematic diagram of a vapor emission test unit (VETU) system in accordance with the present invention for determining the amount of a contaminant emitted in a gas stream being vented at a specified pressure based upon the weight gain of a medium through which a defined amount of the gas stream is passed to separate the contaminant therefrom.

These drawings will be described in detail in connection with the Detailed Description of the Invention which follows.

DETAILED DESCRIPTION OF THE INVENTION

In accordance with the precepts of the present invention, the disclosure to follow describes a method and system therefor for measuring or otherwise monitoring the level of a VOC or other vapor or solid contaminant being emitted in a vented gas stream or the like. A medium, such as an adsorbent, a filter, or the like, is used to separate substantially all of the contaminant from a defined amount of the gas stream. The separated contaminants are concentrated in the medium which exhibits an increase in mass corresponding to the amount of the contaminant in the gas stream.

A basic principle of adsorption is that the amount of uptake, and, accordingly, the weight gain of the adsorbent, is a state property of the adsorbent and the adsorbed component which depends mainly on temperature, the concentration of the component, and, to a lesser extent, on other ambient conditions such as humidity. For example, at 0°, 25°, and 50° C., the loading of toluene on activated carbon is roughly inversely proportional to temperature. Likewise, at a given concentration, loading is directly proportional to absolute pressure, and decreases with humidity, but only significantly above 50% saturation. Thus, even under unsteady-state conditions, the effects of temperature, pressure, and humidity can be considered. For most industrial applications, however, ambient conditions change relatively slowly, i.e., over hours rather than seconds.

An inherent advantage of utilizing adsorption as a separating means is that adsorbents generally concentrate certain compounds by ratios of about 10 to about $10^4$. For example, isotherms at 25° C. may be considered for a typical organic compound, such as toluene, methyl acetate, or dichlorofluoromethane, at a concentration of about 50 ppm. Upon exposure to such compounds at such temperature and concentration, an activated carbon adsorbent will exhibit an increase in mass of about 50 to 200 mg/g (50,000 to 200,000 ppm) depending upon the compound. All but the most volatile organic components, such as methane, effect a similar response in the adsorbent. Moreover, there are available a wide variety of adsorbents both for organic and inorganic compounds, e.g., zeolite 4A for water and light alcohols. Tailored adsorbents even have been engineered to selectively uptake only a certain species from a mixture. Thus, by selecting the type and amount of adsorbent, or by mixing adsorbents, it is possible to manipulate the sensitivity of the adsorbent to be specific to particular airborne contaminants.

Filtration, similarly, exhibits a high selectivity in the separation and retention of solid particles larger than the mean pore size of a filter medium. In basic theory, filtration involves the physical or mechanical removal of solid particles suspended in a fluid of liquid or gas. The porous filter medium retains the particles as a separate phase or filter cake, and passes the clear filtrate. Heretofore, however, the use of filtration as a separating means has been limited by the fact that the pressure drop or resistance to flow through the filter increases as the thickness of the filter cake retained on the filter medium increases. As is detailed hereinafter, the present invention compensates for this increased pressure drop, both for flow through filters as well as for flow through adsorbents, in employing a flow controller, such as a pump, blower, compressor, or the like, to maintain the gas stream being monitored at the pressure at which it is being emitted.

Referring then to FIG. 1, a system according to the present invention for determining the amount of a contaminant, such as a volatile organic compound (VOC), an acid fume, or other vapor or particulate, in a gas or other fluid stream emitted from a vent (not shown) at a specified pressure is shown generally at 10. System 10 may be seen to involve a vessel, shown generally at 12, extending from a flanged portion, 13, to a larger diameter or expanded portion, 14, which may be either of a concentric or an eccentric design. Flanged portion 13 is configured for coupling to the vent and defines an inlet port, 15. Inlet port 15 thereby is coupled in fluid communication with the vented gas stream, represented at 16, which may be a gas stream evolved from a manufacturing, coating, refining, or other process. A defined amount of vented gas stream 16 is received at inlet port 15 for passage through vessel 12 during a measured time interval, t, and contact with an adsorbent or filter medium, 18, which is contained in the larger diameter of the expanded portion 14 of vessel 12. Where gas stream 16 carries a VOC or other vaporous contaminant, it is preferred that medium 18 be provided as a bed of solid particles, such as an activated carbon adsorbent or the like, effective to absorb the VOC thereinto. For acid vapors, such as HCl or HF, a basic medium or an ion exchange resin may be substituted for the activated carbon adsorbent. Alternatively, where gas stream 16 carries a suspended solid particulate contaminant, it is preferred that the medium 18 be provided as a filter having a porosity effective to separate the solid and vapor phases. An outlet port, 20, is provided for exhausting the portion of gas stream 16 passed through vessel 12. Although vessel 12 is shown as being vertically oriented for a generally upwards fluid flow, it will be appreciated that the orientation of vessel 12 may be varied accordingly to space or other design consideration to effect a downwards or even a generally horizontal flow of fluid therethrough.

Medium 18, in whatever form, is provided in vessel 12 in an amount effective for separating substantially all of the contaminant from the defined amount of gas stream 16 passed therethrough. That is, there is no "breakthrough" or exhaustion of medium 18. In this manner, it is assured that the results obtained are meaningful insofar as an accurate measurement could not be verified were a portion of the contaminants in gas stream 16 to pass through vessel 12 without being retained on medium 18. Thus, medium 18, having an initial mass, $m_o$, is made to concentrate the contaminant therein to exhibit a final mass, $m_f$, corresponding to initial mass $m_o$ plus the mass of the contaminant concentrated therein. With variables $m_o$ and $m_f$ being determined, for example, by weighing medium 18 prior to and after contact with gas stream 16, and with the time interval, t, being measured, the amount of the contaminant emitted per unit time in gas stream 16 may be determined according to the expression:

$$\frac{m_c}{t} \qquad (1)$$

where $m_c$ is mass of the contaminant concentrated in the medium defined as the difference $m_f - m_o$.

Where a metered volume of gas stream 16 is passed through medium 18, the concentration of the contaminant in that metered volume may be determined according to the expression:

$$\frac{m_c}{V_g} \qquad (2)$$

where $V_g$ is the metered volume of gas stream 16 passed through medium 18. Additionally, where substantially all of gas stream 16 is passed through vessel 12 during the time interval, t, the rate at which the contaminant is being emitted may be determined directly according to Eq. 1. If, however, only a portion of vented gas stream 16 is passed through vessel 12 as a metered volume $V_g$, the rate at which the contaminant is being emitted may be determined according to the expression:

$$\frac{V_t}{V_g} \frac{m_c}{t} \qquad (3)$$

where $V_t$ is the total volume of gas stream 16 being vented. Volumes $V_g$ and $V_t$ may be derived from the corresponding flow rates of gas stream 16 which may be measured directly with flow meters or the like. Alternatively, volume $V_g$ may be predicted from an empirical relationship correlating the flow rate of stream 16 to its pressure drop through medium 18.

As is shown in FIG. 1, the interior, 22, of vessel 18 may be divided into a plurality of sections, 24b–d, disposed in a series arrangement intermediate a first section, 24a, disposed adjacent inlet port 15, and a last section, 24e, disposed adjacent outlet port 20. Each of sections 24 contains a portion of medium 18, with the number of sections 24 being selected such that substantially none of the contaminant is concentrated in the last section, i.e., section 24e does not exhibit a weight gain. Again, in this way, it is assured that the results obtained are meaningful insofar as an accurate measurement dictates that substantially none of the contaminant pass through pass through vessel 12 without being retained on medium 18.

Where medium 18 is provided as an adsorbent, sections 24 may be formed from a corresponding number of interlocking trays comprised of a frame and a fine mesh wire screen stretched between the frame for supporting the adsorbent, with an additional screen placed surmounting the last tray to prevent loss of fines. Each of the trays is filled with a portion of medium 18. Once filled, the trays are stacked, placed into the interior 22 of vessel 12, and then sealed to the walls thereof. The number and height of the trays may be varied depending upon the amount of medium 18 needed for the particular application.

Alternatively, each of sections 24 may be formed from internal dividers of a fine mesh wire screen with access to the space between each pair of dividers being provided through a corresponding tap, represented at 26a–e, incorporated into the wall of vessel 12. For monitoring suspended solid particulate contaminants, a series of filters may be substituted for the trays or screens forming sections 24. Each subsequent filter preferably is provided as being successively less porous than each preceding filter to effect a chromatographic-type or sieving separation of the retained particles.

During operation, the process conditions at various locations within vessel 12 may be acquired and displayed in real time with sensor probes or like instrumentation deriving outlet signals proportional to the physical conditions of stream 16. For example, and as is shown at 30a–c, thermocouples, pressure transducers, and humidity sensors may be disposed in fluid communication with stream 16 to measure the inlet pressure, $P_1$, temperature, $T_1$, and humidity, $H_1$, thereof. In like manner, similar instrumentation may be provided as is shown at 32a–c to measure the outlet pressure, $P_2$, temperature, $T_2$, and humidity, H2, of stream 16 after it has been passed through medium 18. A computer may be provided to electronically store the output signals from the sensor instrumentation for later printing or manipulation.

Figure 2:
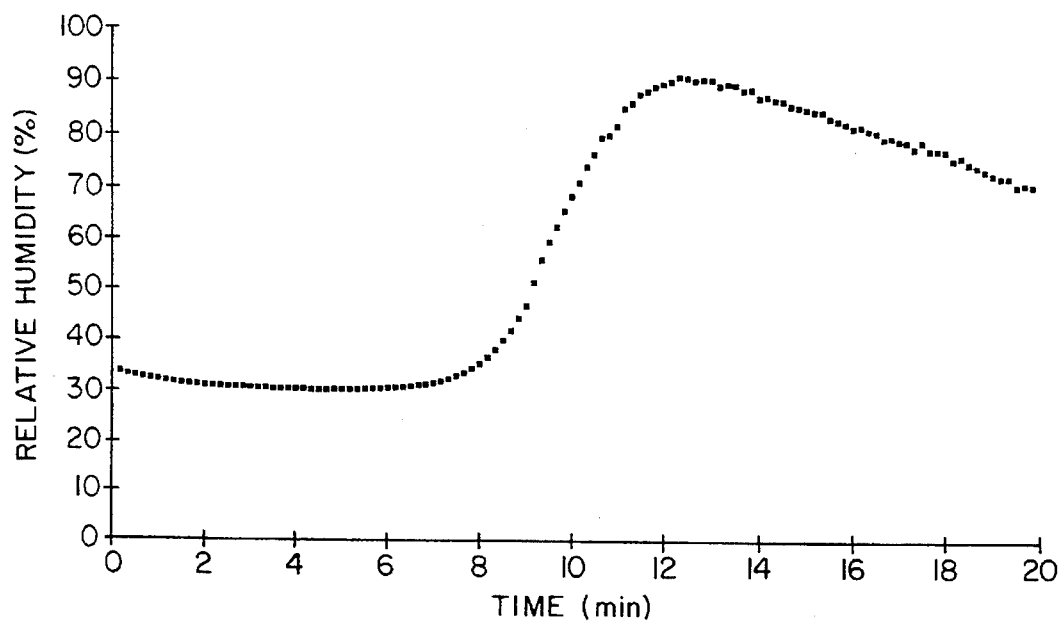
FIG. 2 is a graphical representation illustrating the time dependent behavior of the outlet humidity of the gas stream effluent from the system of the present invention for a constant contaminant concentration.
Figure 3:
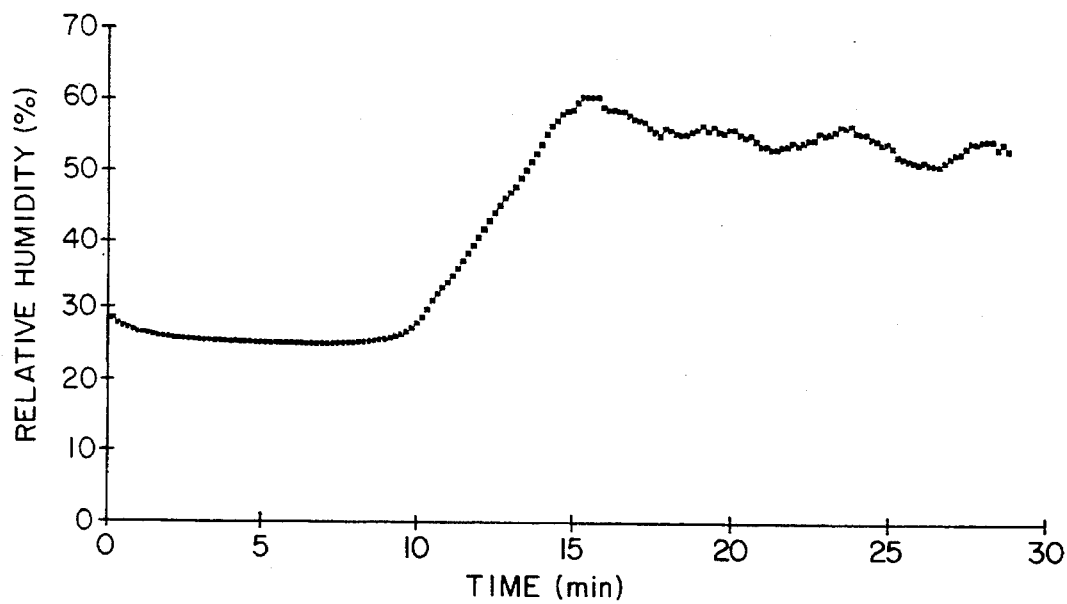
FIG. 3 is a graphical representation illustrating the time dependent behavior of the outlet humidity of the gas stream effluent from the system of the present invention for a variable contaminant concentration.

Additional thermocouples may be introduced into sections 24 to measure, as is shown at 34a–e, the temperature gradient, $T_a$–$T_e$, across medium 18. As the operation of system 10 proceeds, temperature gradient $T_a$–$T_e$ may be used to monitor the exhaustion progression of sections 24. That is, if the temperature in any of sections 24 rises above ambient, there is an indication that the portion of medium 18 therein is being exhausted. The operation of system 10 thereupon may be terminated prior to any breakthrough of the medium 18.

Where stream 16 is vented as a humid air stream and an adsorbent medium 18 is used, it is to be recognized that all adsorbents retain water to some extent, which water is displaced by other, preferentially-adsorbed species such as VOCs. The effect of this displacement is illustrated graphically in FIGS. 2 and 3 which show the time dependent behavior of the outlet humidity of the gas stream effluent from vessel 12 for both constant (FIG. 2) and variable (FIG. 3) contaminant concentrations. Thus, if there is adsorbed water present in medium 18 prior to system 10 being placed on-line, the displacement of that water by the VOC or other contaminant being monitored could affect the analysis. Specifically, as the initial mass $m_o$ of medium 10 would have included the weight of the adsorbed water, the displacement of the adsorbed water could be manifested as an apparent weight loss in the adsorbent. If the humidity and gas flow rate through medium 18 are known, however, the amount of water displaced may be determined, and the weight of its loss may be accommodated for by redefining me, the mass of the contaminant concentrated in the medium, according to the expression:

$$m_f\text{-}(m_o\text{-}H_f) \qquad (4)$$

where $H_f$ is the mass of water vapor in gas stream 16 after passage through vessel 12 and medium 18. The quantity $H_f$ may be derived as the product of humidity $H_2$, and the flow rate, Q, of stream 16 entering vessel 12 at inlet port 15. As is shown at 36, flow rate Q, in turn, may be measured directly with a flow meter or like instrumentation. Alternatively, and as is detailed hereinafter, flow rate Q may be estimated from the pressure drop, $\Delta P$, given as the difference of $P_2$ and $P_1$ as measured, for example, by a differential pressure transducer arrangement.

As aforementioned, prior applications of adsorption or filtration as a separating means have been somewhat limited by in that the pressure drop or resistance to flow through the adsorbent or filter increases with the amount or thickness of the material retained in or on the medium. To compensate for this increased pressure drop, a flow controller, which is represented at 40, is coupled in fluid communication with stream 16 for maintaining the stream at the specified pressure at which it is vented. For gaseous streams 16, flow controller 40 may be provided as a variable-speed blower, compressor, or pump providing a controllable motive force to stream 16 to accommodate for its changing pressure drop through medium 18 or for any flow rate changes or surges in the vent emission. As is shown, flow controller 40 may be located adjacent outlet port 20 to mitigate its effects on the effluent rate from the vent being monitored. Alternatively, flow controller 40 may be located at inlet port 15, or even between a pair of adjacent sections 24, so long as the pressure at inlet port 15 is maintained at the specified pressure, e.g., atmospheric pressure. The set-point and input voltage settings of flow controller 40 may be derived from the signals generated at 30 and 32 by any of a number of known process control methods. With system 10 being configured and operated as described, the amount of the contaminant in stream 16 may be determined without affecting the emission being monitored or otherwise measured.

The example to follow is illustrative of the precepts of the present invention but should not be construed in a limiting sense. All percentages and proportions are by weight, unless otherwise expressly indicated.

EXAMPLE

A vapor emission test unit (VETU) was designed and constructed substantially in accordance with the system described hereinbefore in connection with FIG. 1. An experimental program then was conducted therewith in order to validate the precepts of the present invention, viz., the accurate measurement of a VOC emission. An activated carbon was selected as having a relatively high affinity for most VOCs and a relatively low affinity for water. The contaminants measured, e.g., acetone, hexane, toluene, 1,1,1-trichloroethane, and vinyl acetate, were selected as those being common to many industrial applications.

Each series of tests conducted in the experimental program covered a variety of flow conditions, including both steady-state flow at low and high flow rates, and intermittent flow patterns designed to simulate emissions from cyclic process equipment. The steady-state flow tests resulted in a nearly constant composition, e.g., about 10,000±1000 ppm for toluene, and about 100,000±50,000 ppm for acetone. In contrast, the intermittent flow yielded resulted in a composition range for the influent gas, e.g., from about 0 ppm to about 11,000 ppm for toluene, and from about 0 ppm to about 93,000 ppm for acetone.

Each test in each series was checked for accuracy and repeatability. The tests also included a material balance procedure to confirm that the amount of VOC adsorbed in the VETU was within acceptable limits as compared to the amount of VOC passed into the VETU. This procedure involved evaporating a known quantity of the liquid VOC, and passing this quantity into the VETU for treatment. The weight of the loaded adsorbed was determined, and the effects of any variations in the humidity of the influent and effluent streams were accounted for to ensure rigorous evaluation of the emission rates.

Figure 4:
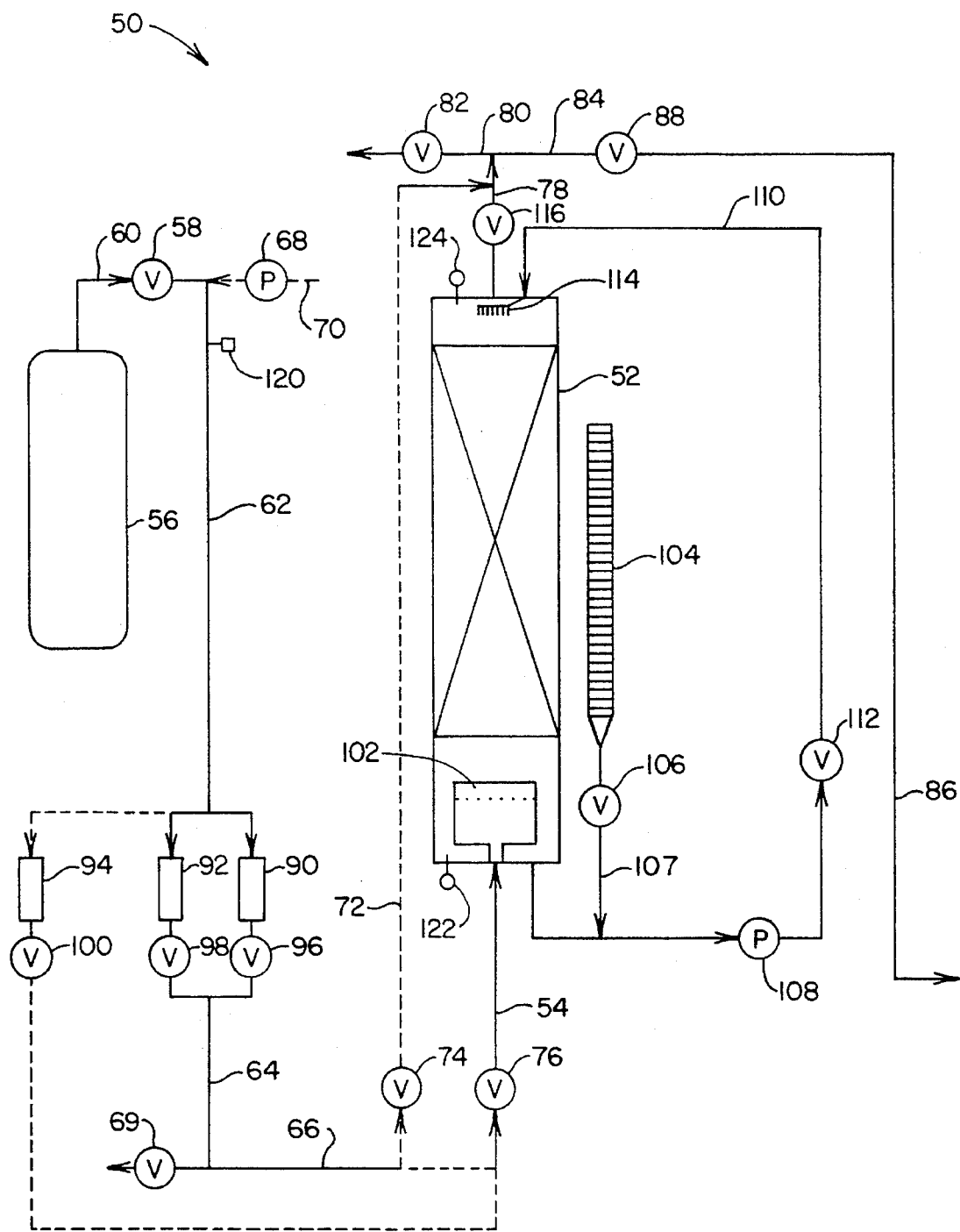
FIG. 4 is a block schematic diagram of a system used to generate a predetermined amount of a vapor-laden gas for validating the precepts of the present invention.

In order to meaningfully evaluate the precepts of the present invention, it was necessary to generate a gas stream, either nitrogen or air, which was contaminated with a measured amount of the VOC liquid. Accordingly, a vapor-laden gas generating system (VLGGS), shown generally at 50 in FIG. 4, was constructed. Looking to FIG. 4, VLGGS 50 may be seen to comprise a vapor generator, 52, in which the liquid VOC contaminant was evaporated. A gas stream of either air or nitrogen was supplied to vapor generator 52 via line 54 from, respectively, a nitrogen cylinder, 56, coupled to line 54 via valve 58 and lines 60, 62, 64, and 66, or an air compressor, 68, coupled to line 54 via lines 70, 62, 64, and 66. For safety considerations, line 66 was provided with a pressure relief valve, 69.

In most of the experiments, viz., Series 1–9, the gas flow from either cylinder 56 or compressor 68 was split via line 72 and valves 74 and 76 such that a portion thereof bypassed generator 52 for venting to the atmosphere via lines 78 and 80 and valve 82, or to the VETU (not shown) via lines 78, 84, and 86 and valve 88. The gas flow rate was monitored through a trio of flow meters, 90, 92, and 94, having associated valves 96, 98, and 100. One of either flow meter 90 or 92 was used for low to moderate flow rates, while both were used for the highest flow rates. For the tests in Series 10 wherein low concentrations of the contaminant were monitored, flow meter 94 was used to admit a small amount of gas to generator 52, with flow meters 90 and 92 used to meter a larger flow which was made to bypass generator 52 via line 72 for passage directly into the VETU.

The nitrogen or air stream from cylinder 56 or compressor 68 was admitted into generator 52 via a perforated cap, 102, which was configured to direct the gas stream uniformly therethrough. As the gas flowed upwardly through generator 52, it was made to countercurrently contact the liquid VOC, at least a portion of which is evaporated into the gas stream. In order to accurately determine the amount which was added into generator 52, the liquid VOC was metered from a buret, 104, having an associated valve, 106, and delivery line, 107. A pump, 108, was used to draw the liquid from buret 104 and through line 110 and valve 112 for admission into generator 52 via a perforated distributor tube, 114, located at the top thereof. To enhance the evaporation of the liquid VOC into the gas stream, generator 52 usually was filled with both structured and unstructured stainless steel packing, although for some tests it was left unpacked. Any excess VOC which was not evaporated into the gas stream was drawn from the bottom of vapor generator via line 110, mixed with virgin VOC from buret 104 and line 107, and then pumped back to generator 52 for re-contact with the gas stream. The vapor-laden gas stream generated in generator 52 was passed therefrom via valve 116 and line 78, whereupon it was mixed with the by-passed gas stream from line 72 for delivery via lines 84 and 86 to the VETU as a contaminated gas stream. As was illustrated in connection with FIG. 1, the VETU was provided with an associated blower to induce gas flow through the adsorbent such that the inlet pressure was maintained at about 0.000±0.002 psig. During the operation of VLGGS 50, the process conditions of the system were monitored with the sensors shown at 120, 122, and 124.

For each test using the VETU/VLGGS described herein, the possible variables were the species and concentration of the contaminant, the adsorbent type, the gas flow rate, and the composition of the gas stream used to carry the contaminant from the VLGGS to the VETU. Of these, only the concentration of the contaminant and the flow rate of the gas were changed within a series of tests, with the remaining variables being held constant. Table 1 summarizes the test conditions for each series.

TABLE 1

SUMMARY OF VOC TEST CONDITIONS

| Series | Adsorbent | Mesh Size | Contaminant | Gas |
|---|---|---|---|---|
| 1 | BS/3007[1] | 20 × 50 | Acetone | Air |
| 2 | BS/3007 | 20 × 50 | n-Hexane | Air |
| 3 | BS/3007 | 20 × 50 | Toluene | Air |
| 4 | BS/3007 | 20 × 50 | Azeotrope[3] | $N_2$ |
| 5 | BS/3007 | 20 × 50 | Vinyl Acetate | $N_2$ |
| 6 | BS/3007 | 20 × 50 | 1,1,1 Trichloroethane | $N_2$ |
| 7 | BS/3007 | 20 × 50 | Vinyl Acetate + $H_2O$[4] | $N_2$ |
| 8 | BS/3007 | 20 × 50 | Vinyl Acetate + $H_2O$ | Air |
| 9 | BS/3007 | 20 × 50 | 1,1,1 Trichloroethane | Air |
| 10 | BS/3007 | 20 × 50 | Toluene | Air |
| A | BS/3007 | 20 × 50 | Acetone | $N_2$ |
| B | BS/AC[2] | 6 × 12 | n-Hexane | $N_2$ |
| C | BS/3007 | 20 × 50 | n-Hexane | $N_2$ |
| D | BS/3007 | 20 × 50 | n-Hexane | $N_2$ |
| E | BS/3007 | 20 × 50 | Azeotrope | $N_2$ |

[1]Barneboy & Sutcliffe 3007 ™ activated carbon adsorbent.
[2]Barnabey & Sutcliffe AC ™ activated carbon adsorbent.
[3]Liquid mixture at the azeotropic composition of acetone, n-hexane, and toluene, 38%, 38%, and 24%, respectively. Evaporation, however, caused the composition to drift towards a significantly greater content of toluene in the residual liquid.
[4]Liquid mixture of 40.5% vinyl acetate and 59.5% water. Evaporation of this mixture, however caused the composition to drift towards a significantly greater content of water in the residual liquid.

As is shown in Table 1, Series 1 through 9 followed a common pattern, but each employed a different VOC or carrier gas. Accordingly, these tests compared the suitability of the present invention to measure different types of contaminants under virtually identical conditions. Series 10, however, focused on low contaminant concentrations, e.g., down to 100 ppm.

Essentially all of the test results are reported herein, even those which were obviously flawed. In this regard, it occasionally was necessary to make modifications to the test equipment in order to reduce the more obvious sources of error. For example, Series 4 was the first in which the composition of the residual liquid varied during each experiment. As a result, changes were made as between several of the first six tests in that series to permit the determination of the composition shift, which shift was reflected in a change in liquid density over and above that caused by evaporative cooling. The density shifts were manifested as discrepancies between the dosed and the measured amounts, which discrepancies were considered significant. Hence, the results of the first six tests of that series are listed separately as Series E.

Furthermore, the tests in Series 1 through 10 represent results which were obtained after procedures were established to conduct reasonably accurate and reproducible validation tests. Sets A through D, however, were preliminary tests which helped to determine whether, for example, acetone was suitable as a contaminant notwithstanding the known tendency of ketones to react with carbon, and to refine the equipment and the testing procedure. Consequently, the values obtained in Series A through E are considered less reliable than those of Series 1 through 10.

Before any experiments were conducted, flow meters 90, 92, and 94 of VLGGS 50 were calibrated, and the volume occupied by liquid in generator 52 and its associated tubing was measured. The latter measurement allowed for the inclusion of corrections for density changes due to temperature or composition effects. In order to begin an experiment, three measurements or settings had to be obtained, namely, the gas flow rate, the mass of the liquid contaminant to be added, and the initial mass of the adsorbent. For the vinyl acetate and water experiments, it additionally was necessary to prepare a well mixed dispersion since the two components are essentially immiscible. Table 2 details the steps for a typical experiment.

TABLE 2

TYPICAL TEST PROCEDURE SEQUENCE

Gas Phase

1. Open valves 74 and 82 to allow system 50 to vent to the atmosphere.
2. Close valves 76 and 116 to isolate vapor generator 52.
3. Set gas cylinder 56 or compressor 68 pressure to about 40 psia.
4. Start gas flow by opening valve 58.
5. Adjust needle valve(s) 98, 96 and/or 100 to obtain the desired flow rate, as measured by flow meters 90, 92, and/or 94.

Liquid Phase

1. Add liquid contaminant to buret 104.
2. Allow a portion of the contaminant to enter the bottom of vapor generator 52 by opening valve 106.
3. Actuate pump 108, adjust the speed thereof, open valve 112.
4. Circulate liquid to achieve thermal equilibrium and steady hold-up.
5. Add or remove contaminant by opening valve 106 until the desired level thereof is attained in vapor generator 52; close valve 106.
6. Add to buret 104 the specified amount of liquid contaminant to be fed during the experiment; seal the top of buret 104 loosely with a stopper.
7. Measure the temperature of the contaminant in buret 104.

Solid Phase

1. Weigh the empty adsorbent trays in the VETU.
2. Load the trays with adsorbent.
3. Weigh the trays with loaded with adsorbent.
4. Stack the trays and seal.
5. Position trays in the vessel of the VETU.
6. Connect pressure transducer, blower control lead, and outlet probe in the VETU.

Once the steps enumerated in Table 2 were performed, a test could be commenced. In this regard, valves 74, 76, 116, 82, and 88 were repositioned such that the gas flow entered the adsorbent bed of the VETU. A timer was started, and the speed of the blower in the VETU was adjusted so that there was no appreciable gauge pressure at the entrance of the vessel of VETU. During the experiment, data was recorded and the flow rate and gauge pressure were adjusted to remain constant. The liquid contaminant in buret 104 was admitted such that the liquid level in vapor generator 52 remained fairly constant.

To end an experiment, the gas flow was terminated, and the timer and blower of the VETU were stopped. The temperature at the bottom of generator 52 was recorded, and, for experiments in which the contaminant composition changed, e.g., vinyl acetate + $H_2O$, and the azeotrope, the final density of the contaminant was measured. Lastly, the adsorbent trays were removed from the VETU and individually weighed to determine how much of the contaminant was adsorbed.

As aforementioned, the main criterion used to determine the accuracy of each test was a material balance which accounted for the contaminant to assure that the amount emitted conformed within acceptable limits to the amount collected. Such balance allowed a comparison between the amount of liquid VOC dispensed, and presumably evaporated, and that ultimately collected as vapor as determined by weighing the loaded adsorbent. It additionally was necessary, however, to measure any moisture on the adsorbent and any variations in the humidities of the influent and effluent gas streams, and to adjust the material balance accordingly. For the material balance calculations, the tie point between the VETU and the VLGGS was specified to be at the entrance of the VETU. The material balance around the vapor generator was as follows:

$$\text{liquid added (+ moisture in air)} - \text{liquid remaining} = \text{vapor delivered} \tag{5}$$

where "liquid added" was the mass of any contaminant initially present in vapor generator 52 plus the mass that was added during the experiment, and "liquid remaining" was the mass of the contaminant which remained in vapor generator 52 after the experiment. Where air instead of nitrogen was used as the gas stream, the "moisture in air" term was included to account for the mass of water vapor in the air. In a similar fashion, the material balance around vapor generator 52 was as follows:

$$\text{vapor adsorbed} = \text{final mass} - (\text{initial mass} - \text{moisture in air leaving}) \tag{6}$$

where "final mass" and "initial mass" represent the mass of all of the adsorbent sections in the VETU, and "moisture in air leaving" was determined from the outlet humidity probe of the VETU. The difference between the "vapor delivered" and the "vapor adsorbed," which related directly to the efficiency of the VETU, was termed a "deviation" and was expressed as a percentage as follows:

$$\text{deviation} = (\text{vapor delivered} - \text{vapor adsorbed}) \times 100 / \text{vapor delivered} \tag{7}$$

The "moisture in air" and "moisture in air leaving" terms represent, respectively, the product of the influent and effluent humidities and the gas flow rate. To quantify these terms, it therefore is necessary to determine the gas flow rate. Rather than measuring the gas flow rate directly with a flow meter or the like, it is possible to derive the rate from the measured pressure drop of the gas flow through the adsorbent bed in the VETU, and the number and type of trays loaded with adsorbent therein.

Figure 5:
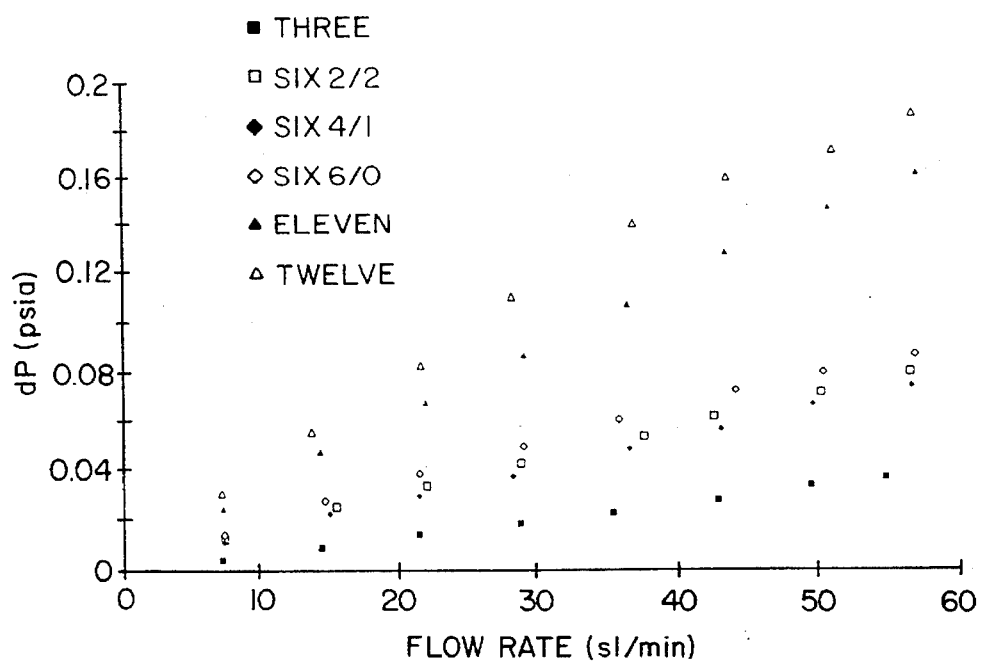
FIG. 5 is a plot of measured pressure drops versus measured gas flows rate through the vapor emission test unit (VETU) of the present invention.

In this regard, an experimental scheme was conducted to correlate the flow rate of the gas stream to its pressure drop through the VETU. The gas flow rate was measured accurately with the electronic flow meters represented at 90 and 92 in FIG. 4. The flow meters were calibrated using a wet test meter to be accurate within ±2%. The pressure drop of the gas through the VETU was measured to within ±0.001 psi. In each experiment, trays of given heights were loaded with activated carbon and weighed. Results of the these experiments are shown in the FIG. 5 as a plot of the measured pressure drop versus the measured flow rate. The specific tray combinations noted therein were as follows:

TABLE 3

KEY TO THE TRAY COMBINATIONS REFERENCED IN FIG. 5

| Name | No. of 1-inch Trays | No. of 2-inch Trays | Overall Height (inches) |
|---|---|---|---|
| Three | 3 | 0 | 3 |
| Six 2/2 | 2 | 2 | 6 |
| Six 4/1 | 4 | 1 | 6 |
| Six 6/0 | 6 | 0 | 6 |
| Eleven | 3 | 4 | 11 |
| Twelve | 4 | 4 | 12 |

Figure 6:
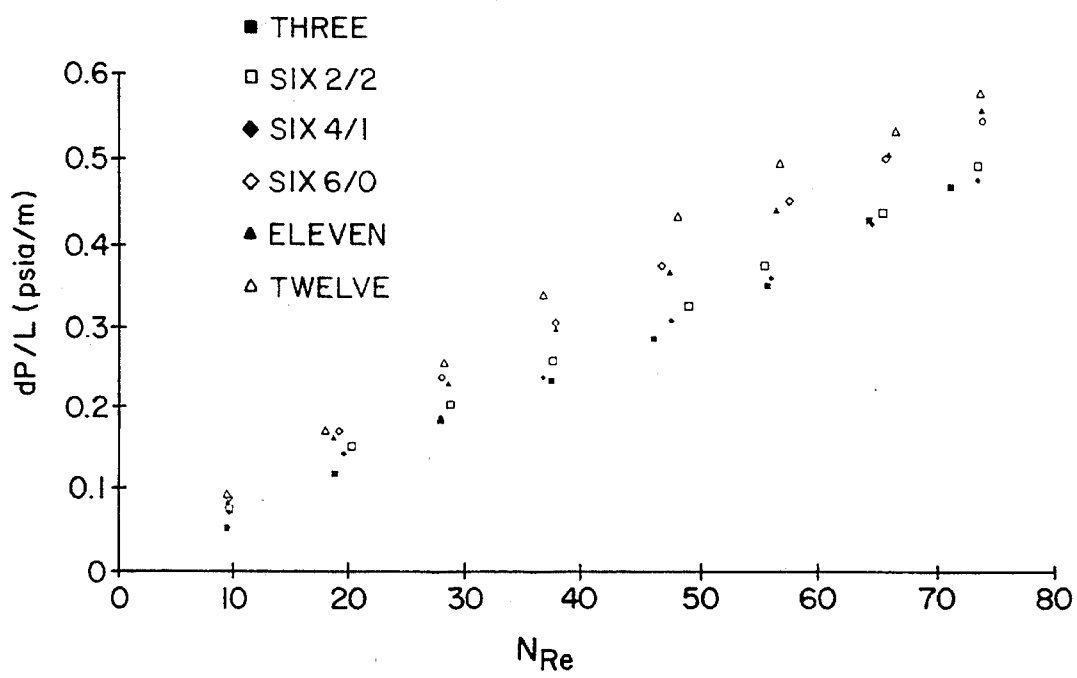
FIG. 6 is a plot of the measured pressure drops versus the Reynolds number ($N_{Re}$) of the gas flows through the vapor emission test unit (VETU) of the present invention.

The height of activated carbon in each tray was determined from its weight and the cross-sectional area of the tray. According to known principles of fluid mechanics, i.e., the Ergun equation, the pressure drop of a fluid flowing through a packed bed, such as the activated carbon in each tray of the VETU, is proportional to the height of the bed. Thus, it is possible to normalize the pressure drop measurements from each of the experiments by dividing the measured pressure drop by the corresponding bed height. It is speculated that variations in the normalized values may be due to small differences in gas density caused by variations in ambient temperature. However, it is possible to mitigate this factor by using the Reynolds number, NRe, which number is a lumped-sum parameter defined as:

$$N_{Re} = \rho \ v \ d_p / \mu \quad (8)$$

where $\rho$ is the gas density, $\mu$ is the gas viscosity, $v$ is the gas superficial velocity, and $d_p$ is the average particle diameter, i.e., 0.025 inch (0.635 mm), of the activated carbon in the adsorbent bed. Although the results are shown in FIG. 6, it may be seen that this correlation alone is insufficient to adequately represent all of the data.

Figure 7:
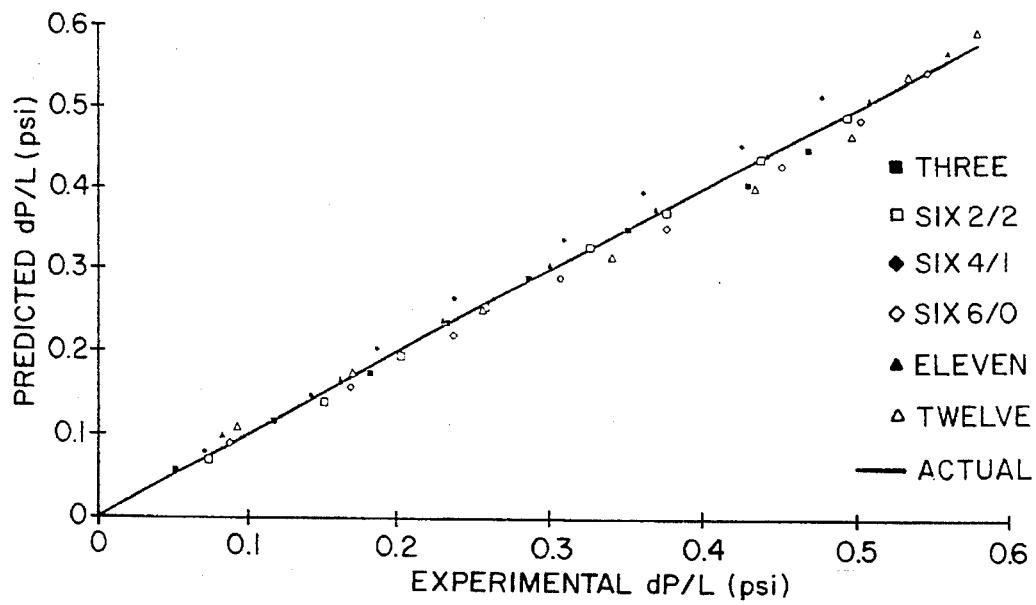
FIG. 7 is a plot of predicted versus the measured pressure drops of the gas flows through the vapor emission test unit (VETU) of the present invention.

As the adsorbent beds are relatively shallow and are covered with a fine retaining screen of approximately 200 mesh having an average opening of 0.003 inch, it is reasonable to assume that there is a pressure drop associated with the gas stream entering and leaving each of the trays. Based on this assumption, and on the observed linear dependence of pressure drop on flow rate or Reynolds number, the following empirical equation was derived to represent the experiment data:

$$dP/L = (a+b \ N_{Re}) + (a'+b'N_{Re})n \quad (9)$$

where n is the number of trays and the coefficients a, b, a', and b' are −0.0285, 1.725, 0.00833, and 0.07410, respectively. Using Eq. 9, pressure drops were predicted for the measured gas flows of the experiments. FIG. 7 shows an agreement well within experimental error between the predicted and the measured pressure drops.

Figure 8:
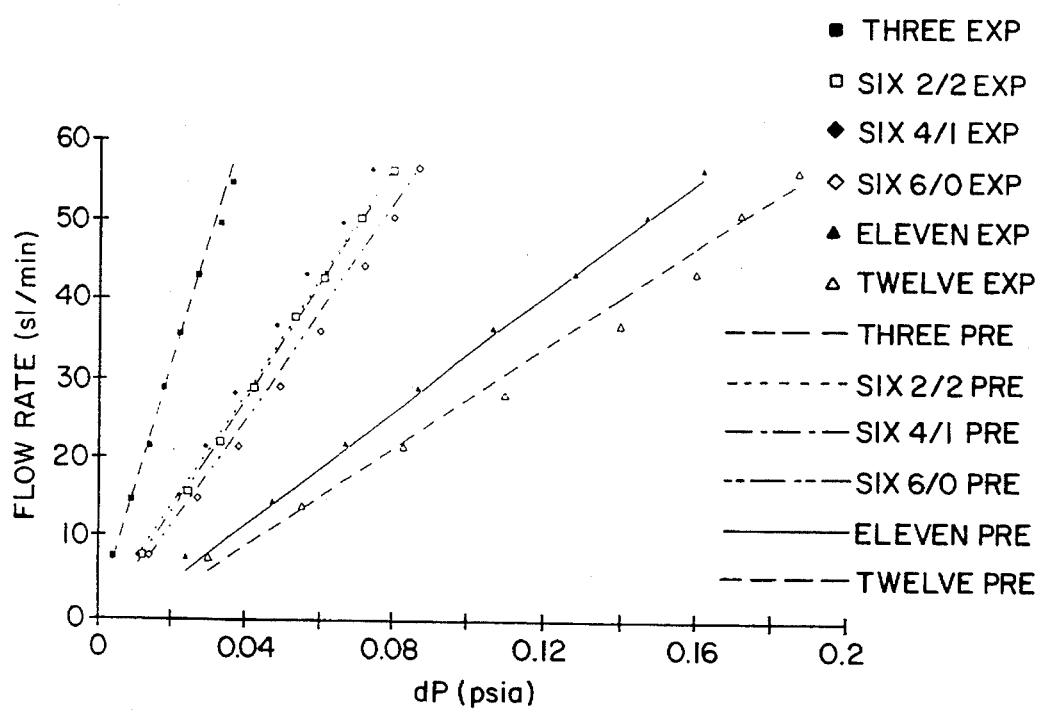
FIG. 8 is a plot of predicted and experimental gas flow rates versus the measured pressure drops of the gas flows through the vapor emission test unit (VETU) of the present invention.

A final confirmation of the validity of Eq. 9 was to determine whether it was possible to predict a flow rate from a measured drop, given the number of trays and the height of activated carbon in the VETU. As is shown in FIG. 8, the predicted and experimental results were in agreement within an average of ±5.5%. Accordingly, it is confirmed that it is possible to accurately predict the instantaneous gas flow rate based on the measured pressure drop of the gas flow through the VETU.

Figure 9:
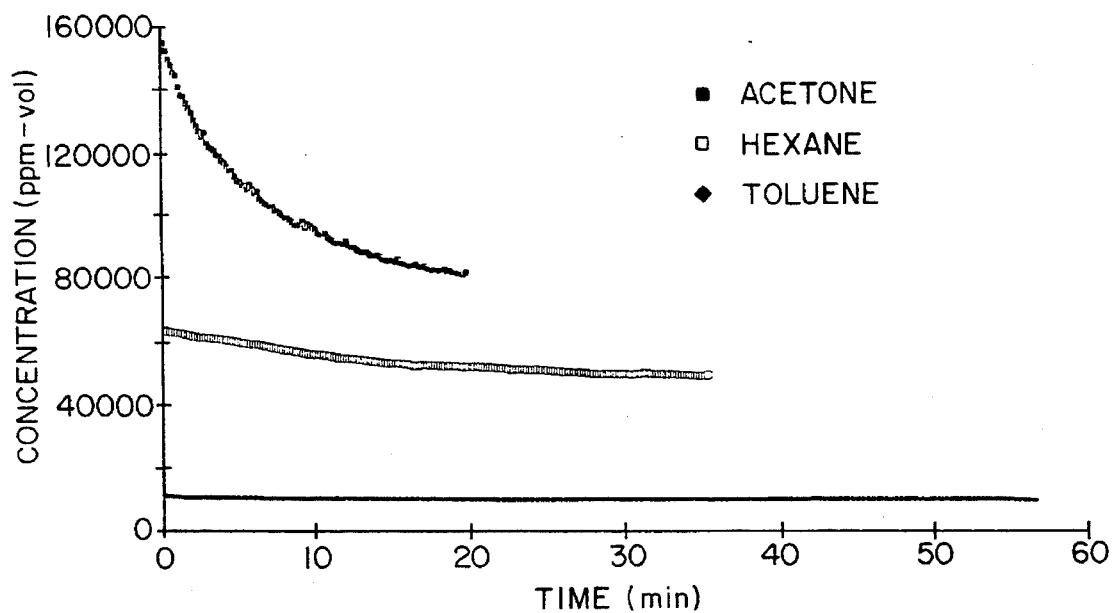
FIG. 9 graphically represents as a plot of concentration versus time the concentration histories of the contaminated gas streams of the experimental tests of the Example having a constant gas flow through the vapor en-fission test unit (VETU) of the present invention.
Figure 10:
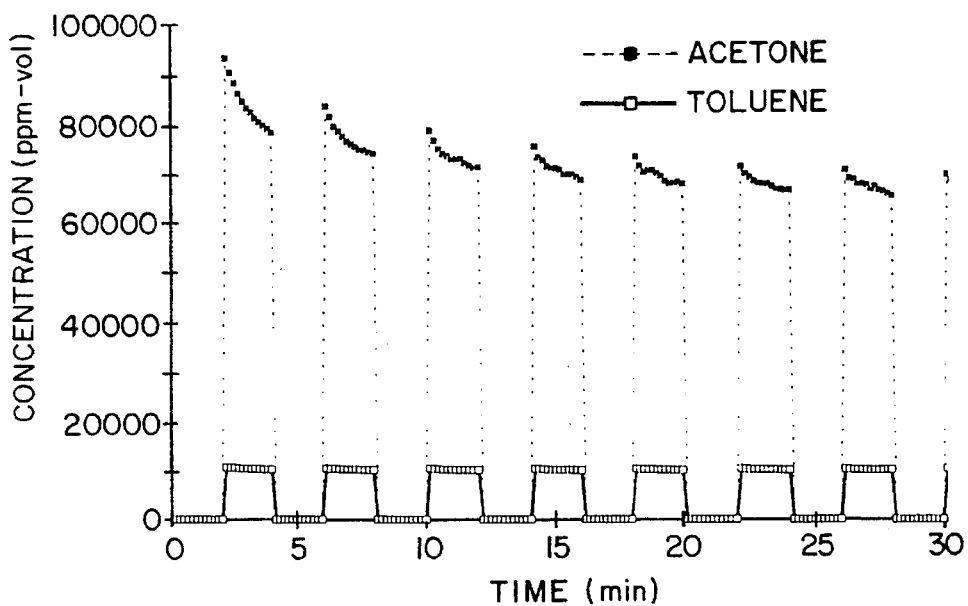
FIG. 10 graphically represents as a plot of concentration versus time the concentration histories of the contaminated gas streams of the experimental tests of the Example having a "pulsed" gas flow through the vapor emission test unit (VETU) of the present invention.

During each of the experiments to follow, the concentration of contaminant in the gas stream entering the VETU was observed to change due to various factors. The most conspicuous factor was the temperature drop caused by the evaporative cooling of the contaminant liquid. For the tests having a constant gas flow, e.g., 1.02, 2.02, and 3.02, representative composition histories of the vapor entering the VETU is shown in FIG. 9. For the tests in which the gas flow was "pulsed," the composition was observed to changed more slowly as the evaporation of the liquid VOC occurred intermittently rather than continuously. Representative concentration histories for the tests having a pulsed gas flow, e.g., 1.05 and 3.05, are shown in FIG. 10. The rate of evaporation, however, appeared to have no appreciable effect on the performance of the VETU apparatus.

The system settings and results for each experiment are listed in Table 4. The following definitions explain the column headings for the table:

"Data Set" refers to a number (1–10) or letter (A–E) denoting the series, and a number indicating the specific conditions of the particular experiment. Experiment numbers that are followed by a letter, e.g., 4.01 B, indicate that the experiment was repeated as the prior experiment exhibited a relatively large discrepancy or was otherwise flawed in some respect. In some instances, the Data Set is followed by a letter and a number, e.g., B.06 C3, indicating that the experiment was repeated at a later date.

"Flow Rate" is the contaminant-free gas flow rate in standard liters per minute (sl/min).

"Splits" refers to the gas flow through vapor generator 52 versus the bypass flow. The first number designates the position of bypass valve 74, and the second number designates the position of valve 76, where 0 is fully closed and 1 is fully open. For some experiments, the valves were deliberately opened fully or partially, and then closed in a cyclic manner. These conditions are denoted by "Pulse." By alternating the valve positions in this manner it was possible to induce sharp changes in concentration, with the magnitude of the change dependent on the relative positions of the valves.

For the "Profile" heading:

"Flat" indicates that the valves remained stationary during the experiment;

"A" indicates that the bypass valve 74 was maintained fully open, and that valve 76 was closed for a given period of time, and then fully opened for an equal or shorter period;

"B" indicates that bypass valve 74 was fully opened for a period of time during which valve 76 was closed, following which valve 74 was opened at ⅓ and valve 76 was fully opened for one minute;

"C" indicates that bypass valve 74 was fully opened for a period of time during which valve 76 was closed, following which valve 74 was opened at ⅓ and valve 76 was fully opened for one minute, following which valve 74 was fully opened and valve 76 was opened at ⅓ for one minute; and "D" indicates that the bypass valve 74 was fully opened for 13 minutes while valve 76 was closed, then valve 74 was closed while valve 76 was fully opened for two minutes.

For the experiments denoted by profiles "A", "B", or "C", in order to conserve time and resources, the duration which the gas flow was made to bypass vapor generator 52 was varied depending on the conditions of the test.

"Deviation" refers to the percentage defined hereinbefore in Eq. 7. Where the value shown is positive, the amount adsorbed is indicated to have been less than the amount delivered. Where the value shown is negative, the amount adsorbed is indicated to have been greater than the amount delivered.

"Duration" indicates the time in minutes during which gas flowed through the VETU during each experiment.

"Adsorbent Condition" indicates the history of the adsorbent. The first number indicates the number of trays which contained fresh adsorbent, the second number indicates the number of trays which contained used, but not spent, adsorbent, and the third number indicates the condition of the desiccant, i.e., whether fresh (F), used (U), or not present (N). Fresh adsorbent was always placed at the entrance of the bed of the VETU.

"Water Loss" refers to the mass of water lost during the experiment, as determined by the effluent humidity.

"Average ppm-vol" refers to the average contaminant concentration during the experiment. This concentration was calculated as the moles of contaminant evaporated divided by the moles of gas and water vapor entering the VETU.

TABLE 4

VOC EMISSION MEASUREMENT RESULTS
(*Extraneous Deviations Not Considered in the Statistical Summary)

| Data Set | Flow Rate (sl/min) | Splits | Profile | Deviation (%) | Duration (min) | Adsorbent Condition | Water Loss (g) | Average ppm-vol |
|---|---|---|---|---|---|---|---|---|
| Acetone/Air | | | | | | | | |
| 1.01 A | 21.16 | 1.0/1.0 | Flat | 10.03 | 38 | 5, 0, N | 0.84 | 69400 |
| 1.01 B | 20.28 | 1.0/1.0 | Flat | 8.97 | 31 | 3, 0, N | 4.35 | 66700 |
| 1.01 C | 20.51 | 1.0/1.0 | Flat | 8.20 | 29 | 3, 0, N | 3.86 | 69200 |
| 1.01 D | 21.15 | 1.0/1.0 | Flat | 8.94 | 11 | 2, 1, N | 0.60 | 111400 |
| 1.01 E | 21.08 | 1-0/1.0 | Flat | 9.05 | 13 | 2, 1, N | 1.11 | 99700 |
| 1.02 | 20.87 | 1.0/1.0 | Flat | 7.77 | 19 | 3, 0, N | 3.27 | 101600 |
| 1.03 | 20.56 | 1.0/1.0 | Flat | 8.31 | 20 | 2, 1, N | 3.67 | 98100 |
| 1.04 | 47.87 | 1.0/1.0 | Flat | 7.57 | 10 | 2, 1, N | 3.92 | 81500 |
| 1.05 | 21.15 | Pulse | A | 6.82 | 35 | 2, 1, N | 2.95 | 39400 |
| 1.06 | 20.85 | Pulse | B | 7.90 | 23 | 1, 2, N | 2.74 | 58100 |
| 1.07 A | 20.71 | Pulse | C | 8.10 | 22 | 1, 2, N | 2.60 | 61000 |
| 1.07 B | 21.30 | Pulse | C | 6.94 | 19 | 1, 2, N | 1.44 | 70300 |
| Hexane/Air | | | | | | | | |
| 2.01 A | 21.00 | 1.0/1.0 | Flat | 8.54 | 32 | 5, 0, N | 1.99 | 59900 |
| 2.01 B | 20.23 | 1.0/1.0 | Flat | 7.03 | 33 | 3, 2, N | 2.26 | 60000 |
| 2.02 | 20.53 | 1.0/1.0 | Flat | 7.08 | 36 | 3, 2, N | 5.18 | 54700 |
| 2.03 A | 20.34 | 1.0/1.0 | Flat | 11.78* | 34 | 3, 2, N | 3.87 | 57800 |
| 2.03 B | 20.50 | 1.0/1.0 | Flat | 7.45 | 25 | 3, 0, N | 5.38 | 62100 |
| 2.04 | 47.59 | 1.0/1.0 | Flat | 8.08 | 8 | 2, 1, N | 1.79 | 65500 |
| 2.05 | 20.50 | Pulse | A | 7.68 | 40 | 3, 0, N | 1.48 | 20300 |
| 2.06 A | 20.49 | Pulse | B | 10.01 | 19 | 3, 0, N | 0.36 | 41100 |
| 2.06 B | 20.84 | Pulse | B | 7.08 | 27 | 2, 1, N | 2.08 | 42500 |
| 2.07 A | 20.81 | Pulse | C | 8.27 | 29 | 3, 0, N | 1.15 | 40400 |
| 2.07 B | 20.82 | Pulse | C | 8.28 | 28 | 2, 1, N | 2.78 | 41100 |
| Toluene/Air | | | | | | | | |
| 3.01 | 17.96 | 1.0/1.0 | Flat | 5.99 | 115 | 5, 0, N | −0.54 | 9500 |
| 3.02 | 18.18 | 1.0/1.0 | Flat | 4.86 | 57 | 0, 3, N | 1.58 | 10100 |
| 3.03 | 18.94 | 1.0/1.0 | Flat | 8.08 | 53 | 0, 3, N | 2.35 | 10300 |
| 3.04 | 45.15 | 1.0/1.0 | Flat | 6.74 | 17 | 0, 3, N | 2.61 | 13600 |
| 3.05 | 20.47 | Pulse | A | 3.47 | 96 | 3, 0, N | 1.81 | 5300 |
| 3.06 | 19.88 | Pulse | B | 6.70 | 27 | 1, 2, N | 0.97 | 19100 |
| 3.07 | 19.24 | Pulse | C | 3.59 | 50 | 1, 2, N | 1.46 | 10600 |
| Azeotrope/$N_2$ | | | | | | | | |
| 4.01 G | 27.95 | 1.0/1.0 | Flat | 14.62* | 23 | 5, 0, N | 6.44 | 78100 |
| 4.01 H | 27.95 | 1.0/1.0 | Flat | 8.19 | 26 | 5, 0, N | 8.61 | 67700 |
| 4.02 | 27.95 | 1.0/1.0 | Flat | 8.06 | 29 | 5, 0, N | 9.98 | 60500 |
| 4.03 | 27.95 | 1.0/1.0 | Flat | 8.30 | 29 | 5, 0, N | 10.53 | 61600 |
| 4.04 | 55.47 | 1.0/1.0 | Flat | 8.32 | 13 | 5, 0, N | 9.44 | 67100 |
| 4.05 | 27.95 | Pulse | A | 1.73 | 48 | 3, 2, N | 12.39 | 15000 |
| 4.06 A | 27.95 | Pulse | B | 9.31 | 18 | 3, 0, N | 4.73 | 37900 |
| 4.06 B | 27.95 | Pulse | B | 8.92 | 37 | 5, 0, N | 10.45 | 39100 |
| 4.06 C | 27.95 | Pulse | B | 4.74 | 18 | 3, 0, N | 5.99 | 37900 |
| 4.07 | 27.95 | Pulse | C | 6.91 | 34 | 5, 0, N | 9.66 | 41000 |
| Vinyl Acetate/$N_2$ | | | | | | | | |
| 5.01 A | 27.95 | 1.0/1.0 | Flat | 10.87 | 50 | 3, 3, F | 11.09 | 41000 |
| 5.01 B | 27.95 | 1.0/1.0 | Flat | 8.76 | 45 | 3, 3, F | 13.21 | 45000 |
| 5.01 C | 27.95 | 1.0/1.0 | Flat | 10.11 | 57 | 3, 3, F | 3.21 | 36300 |

TABLE 4-continued

VOC EMISSION MEASUREMENT RESULTS
(*Extraneous Deviations Not Considered in the Statistical Summary)

| Data Set | Flow Rate (sl/min) | Splits | Profile | Deviation (%) | Duration (min) | Adsorbent Condition | Water Loss (g) | Average ppm-vol |
|---|---|---|---|---|---|---|---|---|
| 5.01 D | 27.95 | 1.0/1.0 | Flat | 5.87 | 59 | 4, 0, F | 11.93 | 35600 |
| 5.02 | 27.95 | 1.0/1.0 | Flat | 5.91 | 61 | 3, 1, N | 8.61 | 34500 |
| 5.03 | 27.95 | 1.0/1.0 | Flat | 6.40 | 127 | 2, 4, N | 20.48 | 33100 |
| 5.04 | 55.47 | 1.0/1.0 | Flat | 5.89 | 35 | 4, 0, N | 14.48 | 30500 |
| 5.05 | 27.95 | Pulse | A | 7.29 | 97 | 3, 0, N | 8.81 | 8900 |
| 5.06 A | 27.95 | Pulse | B | 6.67 | 49 | 3, 0, N | 10.00 | 17600 |
| 5.06 B | 27.95 | Pulse | B | 10.18 | 42 | 3, 0, N | 8.05 | 19800 |
| 5.07 | 27.95 | Pulse | C | 7.90 | 35 | 1, 2, N | 6.38 | 23500 |
| | | | | 1,1,1 Trichloroethane/$N_2$ | | | | |
| 6.01 A | 27.95 | 1.0/1.0 | Flat | 11.01 | 38 | 7, 0, N | 7.24 | 50000 |
| 6.01 B | 27.95 | 1.0/1.0 | Flat | 8.12 | 43 | 5, 0, N | 9.98 | 43800 |
| 6.02 | 27.95 | 1.0/1.0 | Flat | 7.14 | 40 | 0, 5, N | 10.48 | 46700 |
| 6.03 | 27.95 | 1.0/1.0 | Flat | 7.54 | 40 | 5, 0, N | 10.31 | 47500 |
| 6.04 | 55.47 | 1.0/1.0 | Flat | 6.66 | 21 | 5, 0, N | 11.16 | 45700 |
| 6.05 | 27.95 | Pulse | A | 5.21 | 84 | 3, 0, N | 11.40 | 9400 |
| 6.06 | 27.95 | Pulse | B | 4.91 | 36 | 3, 0, N | 8.57 | 21200 |
| 6.07 | 27.95 | Pulse | C | 4.26 | 25 | 3, 0, N | 7.49 | 30500 |
| | | | | Vinyl Acetate + $H_2O/N_2$ | | | | |
| 7.01 A | 27.95 | 1.0/1.0 | Flat | 20.55* | 80 | 5, 0, N | 21.37 | 42700 |
| 7.01 B | 27.95 | 1.0/1.0 | Flat | 9.99 | 27 | 0, 3, N | 11.42 | 65300 |
| 7.01 C | 27.95 | 1.0/1.0 | Flat | 3.69 | 127 | 0, 3, N | 33.59 | 16800 |
| 7.02 | 27.95 | 1.0/1.0 | Flat | 12.56* | 59 | 0, 3, N | 20.79 | 33700 |
| 7.03 A | 27.95 | 1.0/1.0 | Flat | 3.40 | 59 | 0, 3, N | 17.72 | 31000 |
| 7.03 B | 27.95 | 1.0/1.0 | Flat | 2.25 | 68 | 0, 3, N | 20.06 | 27200 |
| 7.04 | 55.47 | 1.0/1.0 | Flat | −3.75 | 65 | 0, 3, N | 26.77 | 14400 |
| 7.05 A | 27.95 | Pulse | A | −12.86* | 96 | 0, 3, N | 16.91 | 11700 |
| 7.05 B | 27.95 | Pulse | A | −9.84 | 42 | 0, 3, N | 5.91 | 12800 |
| 7.05 C | 27.95 | Pulse | A | 1.78 | 98 | 0, 3, N | 13.87 | 13400 |
| 7.06 A | 27.95 | Pulse | B | −7.48 | 61 | 0, 3, N | 14.84 | 21300 |
| 7.06 B | 27.95 | Pulse | B | 3.25 | 42 | 2, 1, N | 11.71 | 31100 |
| 7.07 A | 27.95 | Pulse | C | −7.79 | 55 | 2, 1, N | 13.18 | 23700 |
| 7.07 B | 27.95 | Pulse | C | −3.00 | 54 | 1, 2, N | 12.89 | 24100 |
| | | | | Vinyl Acetate + $H_2O$/Air | | | | |
| 8.01 A | 20.87 | 1.0/1.0 | Flat | 18.19* | 27 | 3, 0, N | 1.36 | 62100 |
| 8.01 B | 20.85 | 1.0/1.0 | Flat | −2.77 | 64 | 3, 0, N | 8.14 | 27200 |
| 8.02 A | 20.85 | 1.0/1.0 | Flat | 12.20* | 42 | 2, 1, N | 4.18 | 40700 |
| 8.02 B | 20.75 | 1.0/1.0 | Flat | 5.68 | 47 | 1, 2, N | 6.44 | 36600 |
| 8.03 | 20.75 | 1.0/1.0 | Flat | 2.09 | 51 | 2, 1, N | 6.32 | 33700 |
| 8.04 A | 35.44 | 1.0/1.0 | Flat | 9.16 | 24 | 2, 1, N | 4.52 | 41700 |
| 8.04 B | 34.67 | 1.0/1.0 | Flat | 2.13 | 34 | 1, 2, N | 6.75 | 30400 |
| 8.05 | 20.59 | Pulse | A | 3.74 | 86 | 2, 1, N | 5.01 | 20800 |
| 8.06 | 20.30 | Pulse | B | 0.23 | 64 | 3, 0, N | 7.35 | 27800 |
| 8.07 | 20.18 | Pulse | C | −0.77 | 71 | 3, 0, N | 6.97 | 25400 |
| | | | | 1,1,1 Trichloroethane/Air | | | | |
| 9.01 A | 21.84 | 1.0/1.0 | Flat | 9.79 | 22 | 0, 3, N | 0.90 | 45000 |
| 9.01 B | 20.99 | 1.0/1.0 | Flat | 6.71 | 66 | 0, 5, N | 7.59 | 38600 |
| 9.02 | 21.08 | 1.0/1.0 | Flat | 6.55 | 61 | 0, 5, N | 7.32 | 41300 |
| 9.03 | 21.06 | 1.0/1.0 | Flat | 6.51 | 63 | 3, 2, N | 8.75 | 40400 |
| 9.04 | 40.72 | 1.0/1.0 | Flat | 6.32 | 30 | 3, 2, N | 8.01 | 43800 |
| 9.05 | 21.03 | Pulse | A | 3.63 | 84 | 3, 0, N | 4.16 | 12500 |
| 9.06 | 20.97 | Pulse | B | 7.51 | 28 | 3, 0, N | 1.92 | 36700 |
| 9.07/ | 20.78 | Pulse | C | 8.01 | 27 | 3, 0, N | 2.91 | 38200 |
| | | | | Toluene/Air | | | | |
| 10.01 | 18.02 | | Flat | 8.50 | 29 | 3, 0, N | 0.88 | 19400 |
| 10.02 | 17.56 | | Flat | 4.15 | 57 | 1, 2, N | 1.54 | 10200 |
| 10.03 | 16.65 | | Flat | 2.16 | 127 | 1, 2, N | 2.66 | 4900 |
| 10.04 | 18.46 | | Flat | 1.59 | 109 | 1, 2, N | −2.87 | 2600 |
| 10.05 | 20.14 | | Flat | 1.85 | 111 | 1, 2, N | 2.92 | 3600 |
| 10.06 | 20.17 | | Flat | 2.52 | 118 | 1, 2, N | 1.55 | 1200 |
| 10.07 | 47.95 | | Flat | −3.92 | 132 | 1, 2, N | 5.70 | 499 |
| 10.08 | 46.19 | | Flat | −3.15 | 142 | 1, 2, N | 2.75 | 166 |
| 10.09 | 47.52 | | Flat | −3.50 | 196 | 1, 2, N | 6.29 | 113 |
| 10.10 | 47.05 | | Flat | −4.45 | 124 | 1, 2, N | 4.44 | 185 |
| 10.11 | 47.19 | | Flat | −6.27 | 127 | 1, 2, N | 4.36 | 177 |
| 10.12 | 47.22 | | Flat | −7.57 | 381 | 1, 2, N | 4.49 | 61 |
| 10.13 | 18.20 | Pulse | D | 2.82 | 105 | 1, 2, N | 3.10 | 4600 |
| 10.14 | 18.74 | Pulse | D | 3.00 | 105 | 1, 2, N | 2.82 | 4600 |

TABLE 4-continued

VOC EMISSION MEASUREMENT RESULTS
(*Extraneous Deviations Not Considered in the Statistical Summary)

| Data Set | Flow Rate (sl/min) | Splits | Profile | Deviation (%) | Duration (min) | Adsorbent Condition | Water Loss (g) | Average ppm-vol |
|---|---|---|---|---|---|---|---|---|
| | | | Acetone/$N_2$ | | | | | |
| A1 | 27.95 | 1.0/1.0 | Flat | 6.12 | 9 | 3, 3, F | 6.97 | 108500 |
| | | | Hexane/$N_2$ | | | | | |
| B.01 | 27.95 | 0/1.0 | Flat | unknown | 36 | 7, 0, N | — | — |
| B.02 | 15.84 | 0/1.0 | Flat | 2.54 | 29 | 7, 0, N | 4.18 | 102200 |
| B.03 | 8.00 | 0/1.0 | Flat | 3.75 | 51 | 7, 0, N | 3.85 | 109200 |
| B.04 | 27.75 | 0.3/1.0 | Flat | 5.83 | 21 | 7, 0. N | 3.59 | 76600 |
| | | | Hexane/$N_2$ | | | | | |
| C.01 | 27.95 | 0.3/1.0 | Flat | unknown | 22 | 7, 0, N | 2.70 | — |
| C.02 | 27.95 | 0.5/1.0 | Flat | 15.31 | 21 | 7, 0, N | 2.57 | 75000 |
| C.03 | 27.95 | 0.5/1.0 | Flat | 8.89 | 23 | 3, 4, N | 3.37 | 67800 |
| C.04 | 27.95 | 0.5/1.0 | Flat | 11.63 | 22 | 3, 4, N | 4.18 | 67200 |
| C.05 | 27.95 | 1.0/1.0 | Flat | 14.08 | 50 | 3, 4, N | 8.42 | 30700 |
| C.06 | 27.95 | 1.0/1.0 | Flat | 1.30 | 45 | 3, 3, F | 22.70 | 34100 |
| C.06 C3 | 27.95 | 1.0/1.0 | Flat | 5.50 | 24 | 0, 3, N | 9.61 | 60400 |
| C.06 C5 | 27.95 | 1.0/1.0 | Flat | 8.00 | 26 | 0, 5, N | 5.97 | 56100 |
| C.06 C7 | 27.95 | 1.0/1.0 | Flat | 6.77 | 25 | 0, 7, N | 5.13 | 58500 |
| C.07 | 41.71 | 0.5/1.0 | Flat | 9.39 | 16 | 3, 3, F | 5.52 | 64200 |
| C.08 | 41.71 | 1.0/1.0 | Flat | 8.02 | 23 | 3, 3, U | 11.71 | 44900 |
| C.09 A | 41.71 | 1.0/1.0 | Flat | 10.56 | 23 | 6, 0, F | 7.79 | 43800 |
| C.09 B | 41.71 | 1.0/1.0 | Flat | 12.40 | 23 | 2, 4, U | 0.14 | 44000 |
| C.09 C | 41.71 | 1.0/1.0 | Flat | 5.83 | 23 | 1, 5, U | 14.06 | 43600 |
| C.10 | 55.47 | 0.5/1.0 | Flat | 5.01 | 14 | 3, 3, U | 8.67 | 53600 |
| C.11 | 55.47 | 1.0/1.0 | Flat | 5.91 | 18 | 6, 0, F | 8.82 | 41500 |
| C.11 C5 | 55.47 | 1.0/1.0 | Flat | 6.38 | 13 | 0, 5, N | 7.63 | 56800 |
| | | | Hexane/$N_2$ | | | | | |
| D.01 A | 27.95 | Pulse | A | −17.53 | 70 | 3, 3, U | 23.50 | 8300 |
| D.01 B | 27.95 | Pulse | A | 3.05 | 61 | 1, 5, U | 9.95 | 10300 |
| D.01 C3 | 27.95 | Pulse | A | 1.57 | 54 | 0, 3, N | 12.55 | 11400 |
| D.02 A | 27.95 | Pulse | B | 19.57 | 30 | 1, 5, U | 0.86 | 20500 |
| D.02 B | 27.95 | Pulse | B | −13.02 | 37 | 3, 3, F | 23.57 | 21200 |
| D.02 C | 27.95 | Pulse | B | −17.77 | 31 | 1, 5, F | 21.82 | 25100 |
| D.02 D | 27.95 | Pulse | B | 3.05 | 31 | 1, 1, F | 3.80 | 24700 |
| D.03 | 55.47 | Pulse | A | −6.80 | 49 | 1, 5, F | 28.84 | 9700 |
| D.04 | 55.47 | Pulse | B | −5.25 | 31 | 3, 3, F | 20.82 | 15400 |
| D.05 | 27.95 | Pulse | A | 4.65 | 48 | 1, 1, F | 3.33 | 12900 |
| D.06 | 27.95 | Pulse | A | 4.13 | 48 | 1, 1, F | 3.89 | 12900 |
| D.07 | 27.95 | Pulse | A | 4.68 | 48 | 1, 1, F | 3.12 | 12900 |
| D.08 | 27.95 | Pulse | A | 3.21 | 26 | 0, 2, F | 3.73 | 24200 |
| D.09 | 27.95 | Pulse | C | 6.47 | 23 | 0, 2, F | 3.02 | 26200 |
| D.09 C3 | 27.95 | Pulse | C | 5.46 | 19 | 0, 3, N | 5.24 | 31500 |
| D.10 | 27.95 | Pulse | C | 5.52 | 24 | 0, 2, F | 4.43 | 26100 |
| D.11 | 27.95 | Pulse | C | 4.83 | 60 | 4, 3, F | 17.13 | 25900 |
| | | | Azeotrope/$N_2$ | | | | | |
| E.01 A | 27.95 | 1.0/1.0 | Flat | 16.23 | 19 | 2, 4, F | 4.97 | 100200 |
| E.01 B | 27.95 | 1.0/1.0 | Flat | 9.49 | 21 | 3, 3, F | 9.80 | 81600 |
| E.01 C | 27.95 | 1.0/1.0 | Flat | 9.33 | 22 | 2, 4, F | 10.34 | 83200 |
| E.01 D | 27.95 | 1.0/1.0 | Flat | 11.21 | 22 | 3, 3, F | 4.80 | 81700 |
| E.01 E | 27.95 | 1.0/1.0 | Flat | 13.51 | 20 | 3, 3, F | 5.72 | 88700 |
| E.01 F | 27.95 | 1.0/1.0 | Flat | 11.70 | 22 | 3, 3, F | 3.85 | 81600 |

Figure 11:
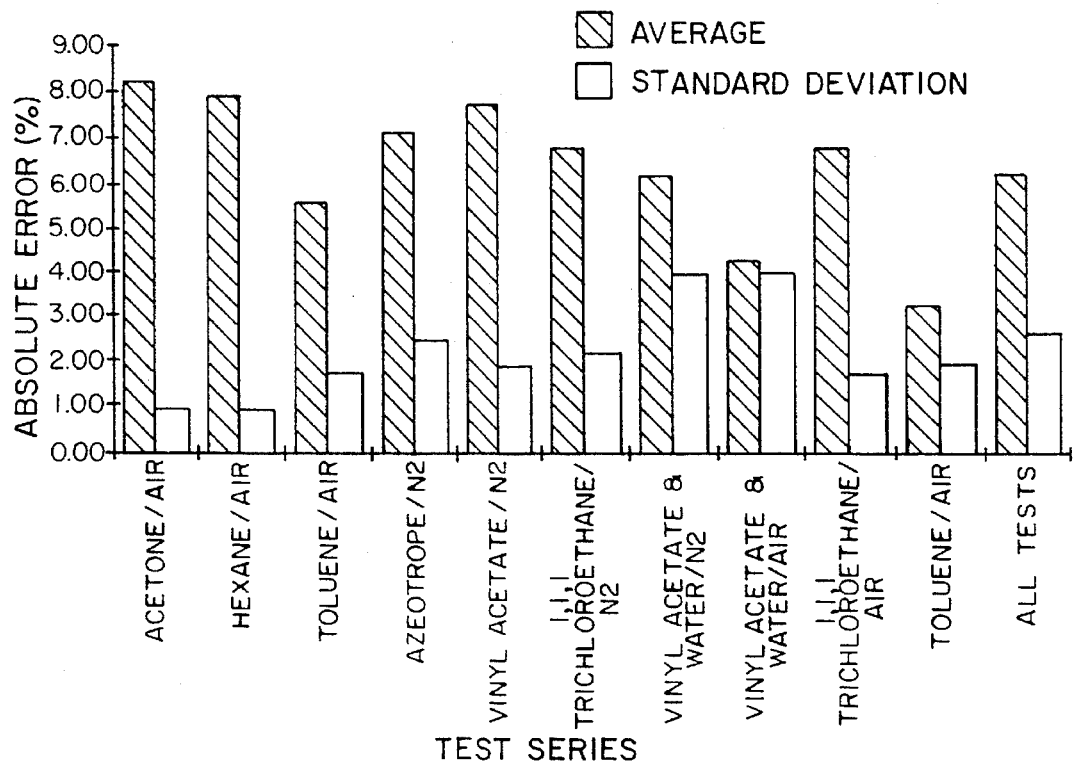
FIG. 11 is a statistical summary presented in bar chart form showing the average and standard deviations for the "deviations" of the test series of the Example.
Figure 12:
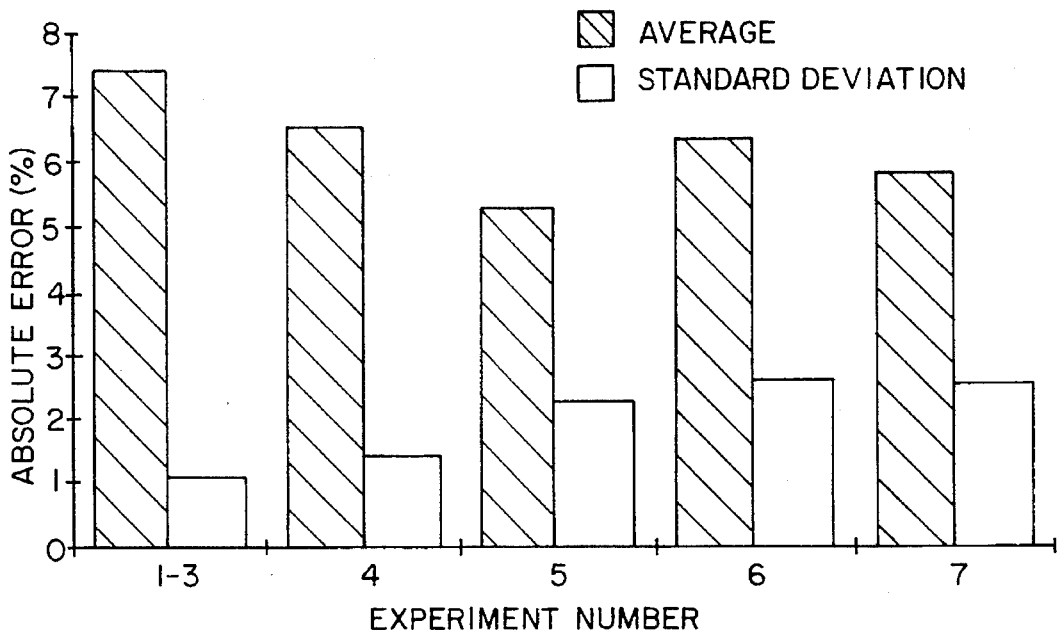
FIG. 12 is statistical summary presented in a bar chart form showing the average and standard deviations by experiment number for the "deviations" of the test series of the Example.

The average "deviations" of each series of tests is shown in FIG. 11. A comparison of the "deviations" for tests in different series with the same operating conditions is shown in FIG. 12. Although the "deviations" appear to be rather random in nature, the "deviations" of the tests involving vinyl acetate and water did tend to have relatively larger standard deviations. This tendency is speculated to be linked to the accuracy and speed of response of the humidity probe at the outlet of the adsorbent bed of the VETU. The tests which were conducted after the humidity probe was calibrated were more consistent.

Overall, the results for the more than one hundred experiments conducted in the Series 1–10 of Table 4 showed an average percent deviation of 6.3% and a standard deviation of 2.6%. Six experiments are denoted as extraneous in exhibiting "deviations" which were out of line with the other experiments in the series. These values were not included in the statistical summary of the experiments. The procedure for identifying the extraneous numbers involved calculating the average and standard deviations of the absolute values of the "deviations," including the suspect points, for each series. If the suspect value was not within two standard deviations of the average, i.e., greater than about 11.58%, it then was classified as extraneous and was ignored in the statistical summaries.

Figure 13:
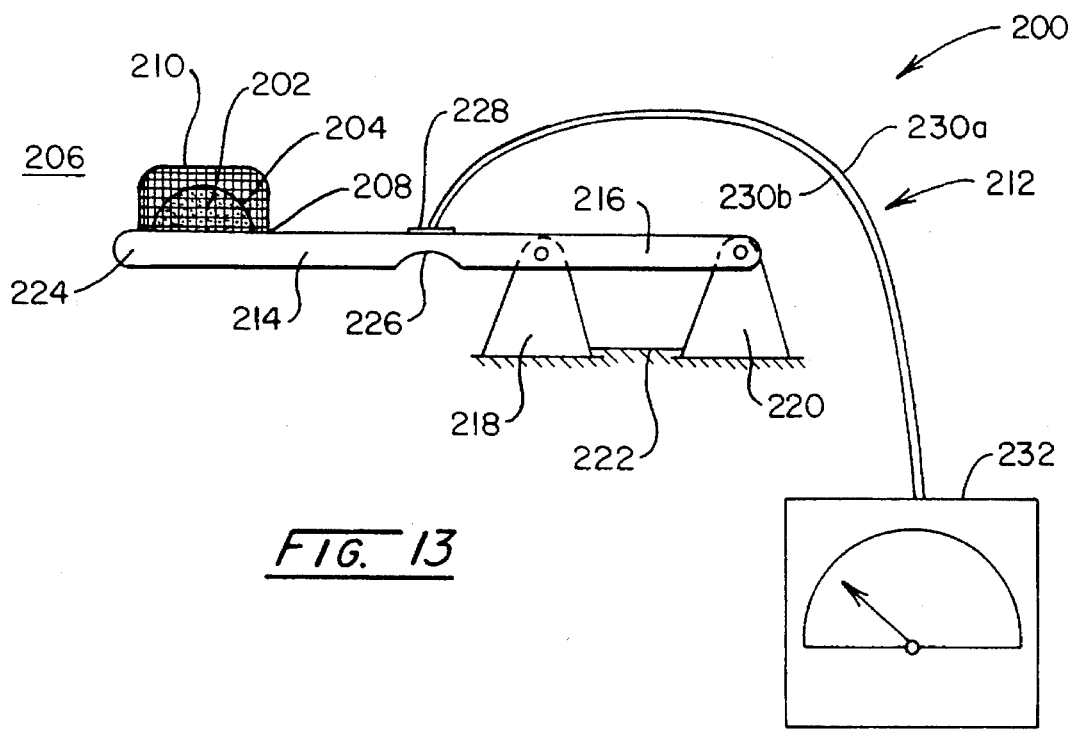
FIG. 13 is a schematic diagram of another system in accordance with the precepts of the present invention for detecting contaminants in a gas emission based upon the weight gain of a medium through which at least a portion of the emission is passed to separate the contaminant therefrom.

Looking next to FIG. 13, an alternative embodiment in accordance with the present invention of a system for detecting, monitoring, or otherwise measuring the level of a VOC or other vapor or solid contaminant contained in a gas emission is shown generally at 200. As did system 10 detailed hereinbefore, system 200 detects contaminants in a gas emission based upon the concentration of the contaminant or contaminants in a separation medium such as an adsorbent or a filter, and the measurement of the increase in weight of the medium, such increase corresponding to the amount of the contaminants in the gas emission. Accordingly, system 200 may be seen to comprise a medium, 202, having at least one surface, 204, in fluid communication with a gas emission, represented at 206, carrying contaminants such as VOCs, acid fumes, suspended particulates, or the like. Where medium 202 is provided as an adsorbent material such as an activated carbon, it preferably is contained in a container, 208, which, as is shown at 210, has a corresponding surface formed of a permeable or transmissive material such as a wire mesh or the like.

For detecting the increase in weight of medium 202 in response to the concentration of the contaminants therein, a sensor assembly, shown generally at 212, is provided. As is shown in the figure, sensor assembly 212 may be provided as comprising a cantilevered member, 214, extending between a fixed end, 216, supported by supports 218 and 220 attached to a frame or housing, 222, and a free end, 224. Free end 224 supports medium 202 such that cantilevered member 214 is deflectable intermediate fixed end 216 and free end 224 in response to the change in mass of medium 202. To amplify the amplitude of the deflection, member 214 may be formed, as is shown at 226, as having a variable cross-section whereat the strain is concentrated. A sensor, 228, is mounted on member 214 and is provided to be responsive to the deflection thereof for generating output signals proportional to the mass of the medium 202. In this regard, sensor 228 may be provided as a strain gauge which generates output signals in response to a change in its internal electrical resistance. The signals generated may be carded by a pair of leads, 230a and 230b, to a display, 232, such as a meter or the like, which is responsive to the signals for displaying indicia corresponding to the amount of the contaminant or contaminants in medium 202. Display 232 additionally may have circuitry for compensating for changes in humidity, temperature, and atmospheric pressure, and for filtering mechanical vibration and electrical noise. Also envisaged is the transmission, via a cable or a transmitter, of the output signals to a control center such that emissions from several sources may be monitored from a central location. Alarms may be provided to indicate the location of each transmission as well as the magnitudes thereof.

Figure 14:
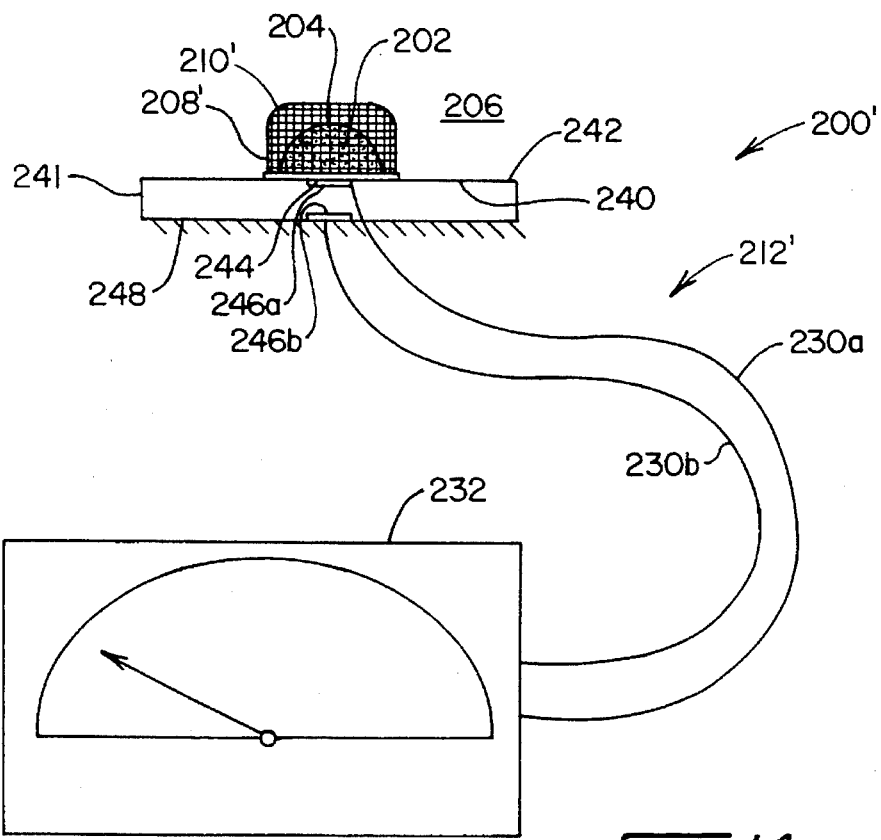
FIG. 14 is a schematic diagram of an alternative embodiment of the system of FIG. 13.

Turning next to FIG. 14, an alternative embodiment of system 200 is shown at 200' to again comprise a medium, 202, having at least one surface, 204, in fluid communication with a gas emission, represented at 206, carrying contaminants such as VOCs, acid fumes, suspended particulates, or the like. As before, where medium 202 is provided as an adsorbent material such as an activated carbon, it preferably is contained in a container, 208', which, as is shown at 210', has a corresponding surface formed of a permeable or transmissive material such as a wire mesh or the like.

As in system 200, a sensor assembly, shown generally at 212', is provided for detecting the increase in weight of medium 202 in response to the concentration of the contaminants therein. In this regard, however, a diaphragm, 240, is provided for supporting medium 202 which diaphragm, in turn, is supported on a frame assembly, 241. Diaphragm 240 has a perimeter, 242, fixed to frame 241 and a central portion, 244, within perimeter 242 which is deflectable in response to the change in mass of medium 202. A first sensor element, 246a, is mounted on central portion 244 for movement in correspondence with the deflection thereof. A second sensor element, 246b, is fixed to a surface or housing, 248, a predetermined distance from first sensor element 246a to confront the movement thereof. With first and second sensor elements 246 being provided, for example, as a pair of parallel capacitance plates, sensor assembly 212' is made to be responsive to the distance therebetween for generating output signals proportional to the mass of the medium 202. Again, the output signals generated may be carried by a pair of leads, 230a and 230b, to a display, 232, such as a meter or the like, which is responsive to the signals for displaying indicia corresponding to the amount of the contaminant or contaminants in medium 202.

It will be appreciated that the methodology associated with systems 200 and 200' is especially suited for detecting fugitive emissions, i.e., inadvertent or sporadic releases, such as might be found at valves, pumps, fittings, or like, caused by inadequate or damaged seals or other defects. Ordinarily, there would be no contaminants in the atmosphere surrounding medium 202 of systems 200 and 200'. Upon being exposed to fugitive emissions, however, the adsorbent or filter thereof would evidence a weight gain resulting from the uptake of the contaminant or contaminants in the emission. For objectively quantifying the emission, the deflection of or the load on sensor assembly 212 or 212' may be calibrated using standardized weights.

While the system of the present invention has been specifically illustrated by reference to FIGS. 1, 4, 13, and 14, the instrumentation, controls, feeders, fittings, pumps, and valves necessary for operation may not have been shown in entirety, but will be understood to be provided in conventional fashion where necessary or desirable. Materials of construction for this system are conventional for the type of operation involved, and will generally be corrosion-resistant, but will depend specifically upon the species of VOC or other contaminant being handled. Piping, duct work and the like will be of similar material and insulated where appropriate. Various of the equipment and lines illustrated can be multiple, series, cascade, or connected in parallel for additional capacity. Regeneration of the adsorbent, filter, or other medium, for example, may be accomplished in conventional fashion.

As it is anticipated that certain changes may be made in the present invention without departing from the precepts herein involved, it is intended that all matter contained in the foregoing description shall be interpreted as illustrative and not in a limiting sense.

What is claimed:

1. A method for determining the amount of a volatile organic compound (VOC) or acid vapor contaminant emitted in a gas stream being vented at a specified pressure from an emission source, said method comprising the steps of:

(a) providing a medium within a vessel having an inlet port coupled in fluid communication with said gas stream for receiving said gas stream at an inlet pressure, and an outlet port for exhausting the gas stream passed through the vessel, said medium being a bed of solid particles effective for separating substantially all of said contaminant from a defined amount of said gas stream;

(b) determining an initial mass, $m_o$, of said medium;

(c) maintaining the inlet pressure of said vessel at said specified pressure of said gas stream being vented from the emission source;

(d) passing through said medium during a time interval, t, said defined amount of said gas stream to concentrate said contaminant in said medium;

(e) determining a final mass, mr, of said medium and said contaminant concentrated therein; and (f) determining the amount of said contaminant emitted per unit time in said gas stream according to the expression:

$$\frac{m_c}{t}$$

where $m_c$ is mass of said contaminant concentrated in said medium defined as the difference $m_f - m_o$.

2. The method of claim 1 further comprising an additional step after step (d) of:

determining the flow rate of said gas stream of step (d) by measuring its pressure drop through said medium.

3. The method of claim 1 wherein said gas stream of step (d) is passed as a metered volume through said medium and which further comprises the step:

(g) determining the concentration of said contaminant emitted in said gas stream according to the expression:

$$\frac{m_c}{V_g}$$

wherein $V_g$ is the metered volume of said gas stream.

4. The method of claim 1 wherein substantially all of said gas stream being vented is passed through said medium in step (d).

5. The method of claim 1 wherein said medium contains adsorbed water, and which further comprises the additional steps of:

measuring the inlet humidity of the gas stream of step (c) before it is passed through said medium;

measuring the outlet humidity of the gas stream of step (d) after it is passed through said medium, wherein the mass of said contaminant concentrated in said medium, $m_c$, is further defined in step (f) according to the expression:

$$m_f - (m_o - H_f)$$

where $H_f$ is the mass of water vapor in the gas stream of step (d) after it is passed through said medium determining the mass of water in said medium from said inlet and said outlet humidity; and subtracting said mass of water from the final mass, $m_f$, of said medium.

6. The method of claim 1 wherein said contaminant emitted in said gas stream is a volatile organic compound (VOC) and said medium is provided as a bed of solid particles effective to adsorb said VOC thereinto.

7. The method of claim 6 wherein said solid particles comprise an activated carbon.

8. The method of claim 1 wherein said contaminant emitted in said gas stream is an acid vapor and said medium is provided as comprising a basic resin effective to remove said acid vapor from said gas stream.

9. The method of claim 1 wherein said medium is provided in said vessel in step (a) in a plurality of sections disposed in a series arrangement intermediate a first section adjacent said inlet port and a last section adjacent said outlet port, each of said sections containing a portion of said medium, and wherein said method further comprises an additional step during step (d) of monitoring the temperature of each said portion of said medium for determining whether any said portion is exhausted, as indicated by notice of any substantial temperature change above ambient that may occur at each said portion.

10. The method of claim 1 wherein said medium is provided in said vessel in step (a) in a plurality of sections disposed in a series arrangement intermediate a first section adjacent said inlet port and a last section adjacent said outlet port, each of said sections containing a portion of said medium, the number of said sections being selected such that the substantially none of said contaminant is concentrated in said last section.

11. A system for determining the amount of a volatile organic compound (VOC) or acid vapor contaminant emitted in a gas stream being vented at a specified pressure, said system comprising:

a vessel having an inlet port coupled in fluid communication with said gas stream for receiving a defined amount thereof at an inlet pressure for passage through said vessel during a time interval, t, and an outlet port for exhausting the gas stream passed through said vessel;

a medium of a bed of solid particles disposed in said vessel for separating substantially all of said contaminant from the defined amount of said gas stream passed through said vessel, said medium concentrating said contaminant therewithin and having an initial mass, $m_o$, and a final mass, $m_f$, corresponding to the mass of said medium and the mass of said contaminant concentrated therein; and a flow controller coupled in fluid communication with said gas stream for maintaining the inlet pressure of said vessel at said specified pressure of said gas stream being vented, wherein the amount of said contaminant emitted per unit time in said gas stream is determined according to the expression:

$$\frac{m_c}{t}$$

where $m_c$ is mass of said contaminant concentrated in said medium defined as the difference $m_f - m_o$.

12. The system of claim 11 wherein said flow controller is a blower which is controllable to force the flow of said gas stream through said vessel at a rate effective for maintaining the pressure of said gas stream being vented at said specified pressure.

13. The system of claim 11 wherein a metered volume of said gas stream is passed through said medium and wherein the concentration of said contaminant emitted in said gas stream is determined according to the expression:

$$\frac{m_c}{V_g}$$

where $V_g$ is the metered volume of said gas stream.

14. The system of claim 11 wherein substantially all of said gas stream being vented is passed through said vessel.

15. The system of claim 11 wherein the interior of said vessel is divided into a plurality of sections disposed in a series arrangement intermediate a first section adjacent said inlet port and a last section adjacent said outlet port, each of said sections containing a portion of said medium, and the number of said sections being selected such that substantially none of said contaminant is concentrated in said last section.

16. The system of claim 11 wherein said contaminant emitted in said gas stream is a volatile organic compound (VOC) and said medium comprises a bed of solid particles effective to adsorb said VOC thereinto.

17. The system of claim 16 wherein said solid particles comprise an activated carbon.

18. The system of claim 11 wherein said contaminant emitted in said gas stream is an acid vapor and said medium comprises a basic resin effective to remove said acid vapor from said gas stream.

19. The system of claim 11 wherein said medium contains adsorbed water and which further comprises:

an inlet humidity sensor disposed in fluid communication with the gas stream being vented for deriving an output signal proportional to the inlet humidity of said gas stream: and an outlet humidity sensor disposed in fluid communication with the gas stream passed through said vessel for deriving an output signal proportional to the outlet humidity of said gas stream, wherein the mass of water vapor in said medium is determined from said inlet and said outlet humidity and is subtracted from the final mass $m_f$, of said medium.

20. The system of claim 11 wherein the interior of said vessel is divided into a plurality of sections disposed in a series arrangement intermediate a first section adjacent said inlet port and a last section adjacent said outlet port, each of said sections containing a portion of said medium and having an associated temperature sensor for monitoring the temperature thereof.

21. A system for detecting contaminants in a gas emission comprising:

a medium effective for separating at least a portion of said contaminants from said gas emission and having at least one surface in fluid communication with said gas emission for concentrating said contaminants therein; and a sensor assembly for sensing the change in mass of said medium in response to the concentration of said contaminants therein, said change in mass of said medium corresponding to the amount of said contaminants in said gas emission, and said sensor assembly comprising:

a cantilevered member extending between a fixed end and a free end supporting said medium, said cantilevered member being deflectable intermediate said fixed end and said free end in response to the change in mass of said medium; and a sensor mounted on said cantilevered member, said sensor being responsive to the deflection of said cantilevered member for generating output signals proportional to the mass of said medium.

22. A system for detecting contaminants in a gas emission comprising:

a medium effective for separating at least a portion of said contaminants from said gas emission and having at least one surface in fluid communication with said gas emission for concentrating said contaminants therein; and a sensor assembly for sensing the change in mass of said medium in response to the concentration of said contaminants therein, said change in mass of said medium corresponding to the amount of said contaminants in said gas emission, and said sensor assembly comprising:

a diaphragm supporting said medium, said diaphragm having a fixed perimeter and a central portion within said perimeter, said central portion being deflectable in response to the change in mass of said medium;

a first sensor element mounted to said central portion of said diaphragm for movement in correspondence with the deflection thereof in response to the change in mass of said medium; and a second sensor element fixed a predetermined distance from said first sensor element to confront the movement thereof, said first and said second sensor element being responsive to the distance therebetween for generating output signals proportional to the mass of said medium.

23. The system of claim 22 wherein said contaminants in said gas stream emission are volatile organic compounds (VOCs) and said medium comprises a bed of solid particles effective to adsorb said VOCs thereinto.

24. The system of claim 23 wherein said solid particles comprise an activated carbon.

25. The system of claim 22 wherein said contaminants in said gas stream emission are acid vapors and said medium comprises a basic resin effective to remove said acid vapors from said gas stream.

26. The system of claim 22 wherein said contaminants in said gas stream emission are suspended particulates and said medium comprises a filter having a porosity effective to remove said particulates from said gas stream.

27. The system of claim 21 further comprising a display responsive to said output signals from said sensor for displaying indicia corresponding to the amount of said contaminant in said medium.

28. The system of claim 21 wherein said sensor is a strain gauge, said output signals being generated in response to a change in the electrical resistance of said strain gauge.

29. The system of claim 22 wherein said first and said second sensor element are configured as a pair of parallel plates, said output signals being generated in response to a change in the electrical capacitance between said plates.

30. The system of claim 22 further comprising a display responsive to said output signals from said first and said second sensor element for displaying indicia corresponding to the amount of said contaminant in said medium.

31. The system of claim 21 wherein said contaminants in said gas stream emission are volatile organic compounds (VOCs) and said medium comprises a bed of solid particles effective to adsorb said VOCs thereinto.

32. The system of claim 31 wherein said solid particles comprise an activated carbon.

33. The system of claim 21 wherein said contaminants in said gas stream emission are acid vapors and said medium comprises a basic resin effective to remove said acid vapors from said gas stream.

34. The system of claim 21 wherein said contaminants in said gas stream emission are suspended particulates and said medium comprises a filter having a porosity effective to remove said particulates from said gas stream.

\* \* \* \* \*